(12) United States Patent
Frazier et al.

(10) Patent No.: US 8,221,384 B2
(45) Date of Patent: Jul. 17, 2012

(54) METHOD OF SECURING A GRAFT

(75) Inventors: Andrew G. C. Frazier, Sunnyvale, CA (US); Michael D. Lesh, Mill Valley, CA (US); Chad C. Roue, Fremont, CA (US); Erik J. van der Burg, Sunnyvale, CA (US)

(73) Assignee: Atritech, Inc., Plymouth, MN (US)

( * ) Notice: Subject to any disclaimer, the term of this patent is extended or adjusted under 35 U.S.C. 154(b) by 0 days.

(21) Appl. No.: 13/270,703

(22) Filed: Oct. 11, 2011

(65) Prior Publication Data
US 2012/0029541 A1    Feb. 2, 2012

Related U.S. Application Data

(60) Continuation of application No. 11/401,036, filed on Apr. 10, 2006, now Pat. No. 8,043,305, which is a continuation of application No. 10/861,691, filed on Jun. 4, 2004, now Pat. No. 7,025,756, which is a continuation of application No. 09/903,970, filed on Jul. 11, 2001, now Pat. No. 6,746,472, which is a division of application No. 09/482,986, filed on Jan. 11, 2000, now Pat. No. 6,328,727, which is a continuation-in-part of application No. 09/399,521, filed on Sep. 20, 1999, now Pat. No. 6,231,561.

(51) Int. Cl.
*A61M 31/00* (2006.01)

(52) U.S. Cl. ...................................... 604/500

(58) Field of Classification Search ............... 604/96.01, 604/101.01, 500, 115, 117, 507, 511; 128/898; 606/139
See application file for complete search history.

(56) References Cited

U.S. PATENT DOCUMENTS

| | | | |
|---|---|---|---|
| 4,872,874 A * | 10/1989 | Taheri | 128/898 |
| 7,025,756 B2 | 4/2006 | Frazier et al. | |
| 2006/0229670 A1 | 10/2006 | Bates | |

* cited by examiner

*Primary Examiner* — Manuel Mendez
(74) *Attorney, Agent, or Firm* — Seager, Tufte & Wickhem LLC

(57) ABSTRACT

Disclosed is an anastomosis catheter, for achieving a tissue to tissue or synthetic graft to tissue attachment. The catheter includes a plurality of deployable tissue anchors, which may be laterally deployed into surrounding tissue. The anchors may be used to achieve end to end or end to side anastomoses. Methods are also disclosed.

16 Claims, 16 Drawing Sheets

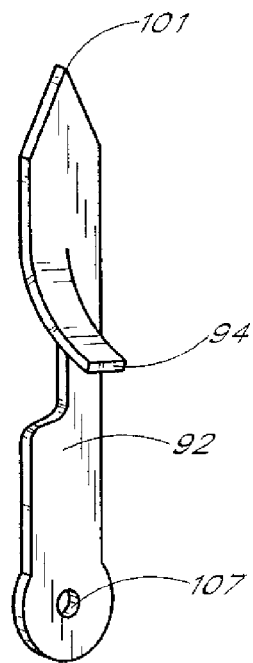
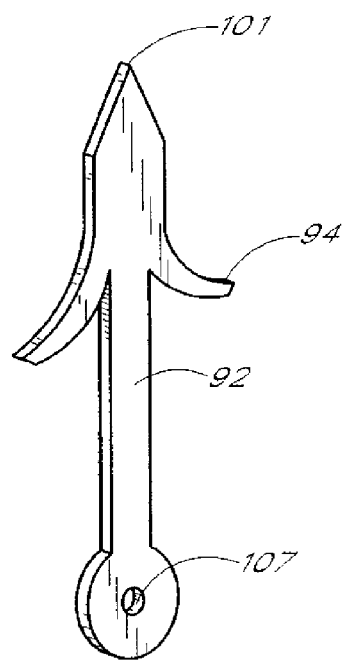
FIG. 15A
FIG. 15B
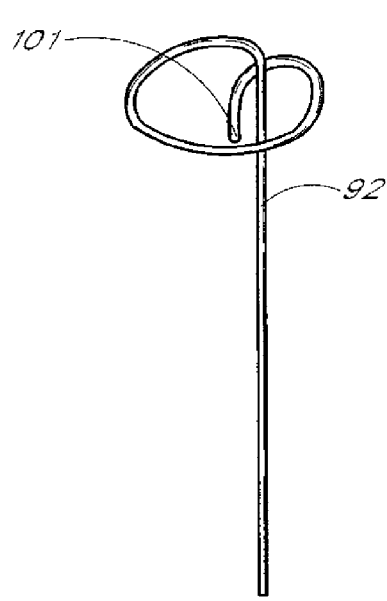
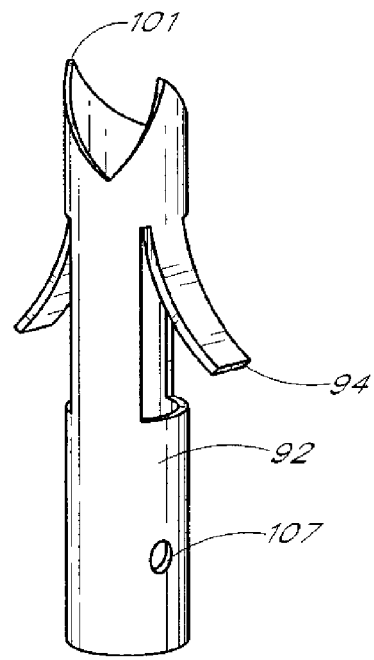
FIG. 15C
FIG. 15D

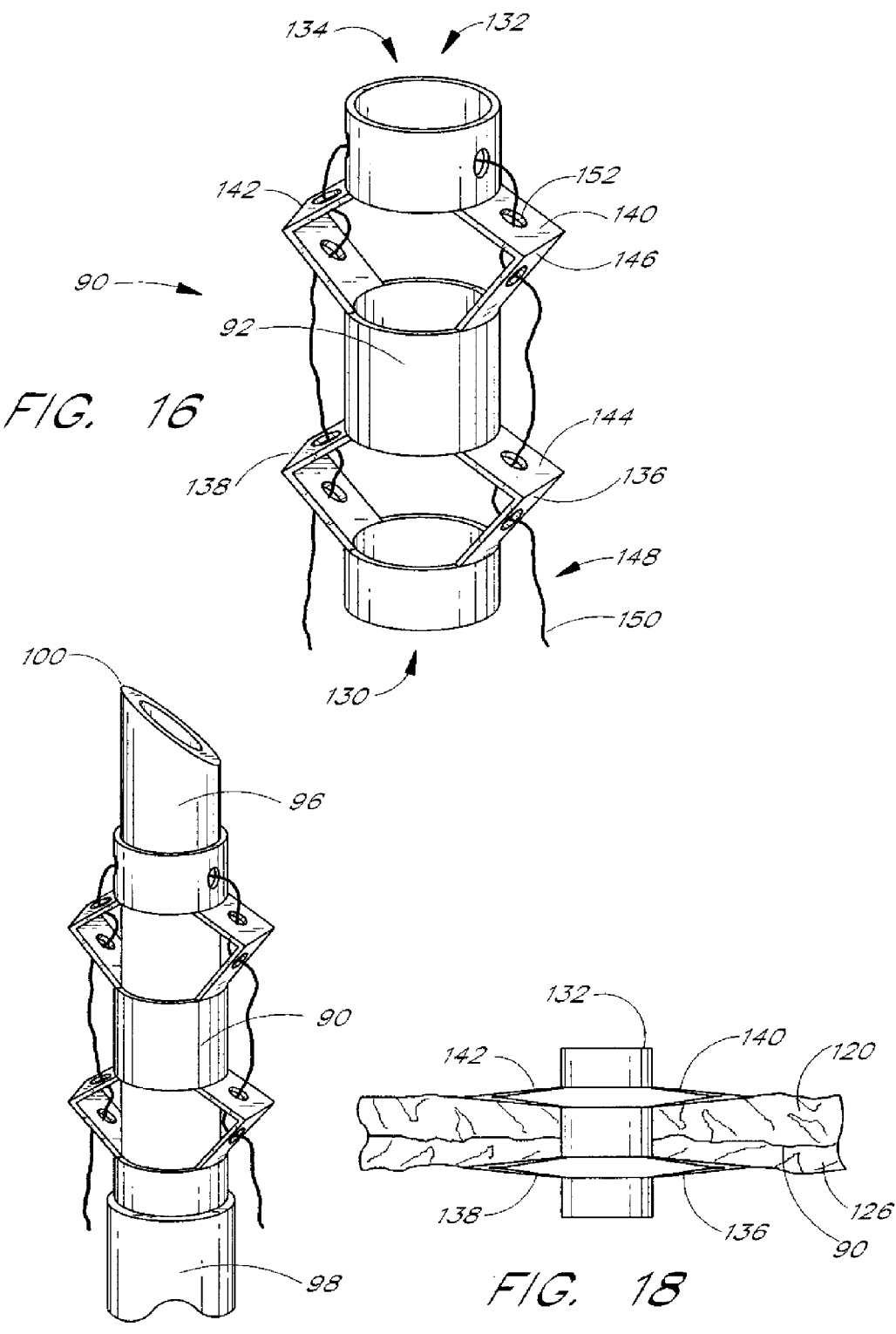

METHOD OF SECURING A GRAFT

RELATED APPLICATIONS

This application is a continuation of application Ser. No. 11/401,036 filed Apr. 10, 2006, which is a continuation of application Ser. No. 10/861,691 filed Jun. 4, 2004, now U.S. Pat. No. 7,025,756, which is a continuation of application Ser. No. 09/903,970 filed Jul. 11, 2001, now U.S. Pat. No. 6,746,472, which is a divisional of application Ser. No. 09/482,986, filed on Jan. 11, 2000, now U.S. Pat. No. 6,328,727, which is a continuation-in-part of application Ser. No. 09/399,521, filed Sep. 20, 1999, now U.S. Pat. No. 6,231,561, the disclosure of which is incorporated in its entirety herein by reference.

BACKGROUND OF THE INVENTION

The present invention relates to methods and devices for performing anastomosis. More particularly, the present invention relates to methods and devices for performing tissue-to-tissue or synthetic graft-to-tissue vascular anastomosis under either direct or transluminal access.

Anastomosis is the union or joinder of one hollow vessel or structure to another so that the interior of the vessels communicate with one another. There are generally two types of vascular anastomosis: end-to-end and end-to-side. In an end-to-end anastomosis, the severed end of a first vessel or an end of a synthetic graft is coupled, usually by suturing or stapling, to the severed end of a second vessel. In the context of a synthetic vascular graft, the ends and possibly intermediate portions of the graft may be secured to the wall of the vessel without removing a portion of the native vessel. In an end-to-side anastomosis, the severed end of a first vessel or an end of a synthetic graft is connected around an opening cut into the side of a second vessel.

Anastomoses are performed in a variety of anatomies, such as between airways, blood vessels, bowels, and urogenital lumens. The procedure for connecting blood vessels is referred to as vascular anastomosis. One of the best known surgical procedures utilizing vascular anastomosis is the coronary bypass. In the context of coronary artery disease, the flow of oxygenated blood to the myocardium of the heart is inhibited by a stenosis or obstruction in the coronary artery. This flow can be improved by providing a coronary artery bypass graft ("CABG") between the aorta and a point in the coronary artery distal to the stenosis. Typically, a section of vein from the leg is removed and attached at one end to the aorta and at the other end to the coronary artery utilizing end-to-side anastomosis. Such grafts are known as saphenous coronary artery bypass grafts. Alternatively, synthetic grafts can be utilized to effect the bypass.

While the typical coronary bypass procedure favorably affects the incidence and severity of angina in patients with coronary artery disease, a variety of risks are associated with such procedures. Among them are mortality, myocardial infarction, postoperative bleeding, cerebrovascular accident, arrhythmias, wound or other infection, aortic dissection and limb ischemia. Furthermore, the vein grafts deteriorate over time, thereby resulting in the recurrence of angina, myocardial infarction and death. In addition, the costs of such procedures are relatively high and the patient recovery relatively long.

In an attempt to overcome such problems, a number of alternative approaches have been developed. For example, artery to artery bypass procedures have been utilized in which an arterial source of oxygenated blood-such as the left internal mammary artery ("LIMA"), right internal mammary artery ("RIMA"), or right internal thoracic artery ("RITA")—is severed and anastomosed to the obstructed coronary artery distally to the stenosis or occlusion. More recently, other arteries have been used in such procedures, including the inferior epigastria arteries and gastroepiploic arteries. In general, artery to artery bypass procedures have demonstrated a better patency rate as compared with autologous vein or synthetic grafts.

While vascular anastomosis can be effective, and sometimes life-saving procedures, traditionally available techniques have been associated with a number of complications. For example, conventional techniques for performing vascular anastomosis generally require an extensive incision in the patient's body. Such operations are traumatic to the patient, involve a lengthy recovery, and a relatively high risk of infection or other complications.

In the context of coronary bypass surgery, for example, the bypass graft or artery-to-artery procedure is traditionally performed using an open chest procedure. In particular, each procedure involves the necessity of a formal 20 to 25 cm incision in the chest of the patient, severing the sternum and cutting and peeling back various layers of tissue in order to give access to the heart and arterial sources. As a result, these operations typically require large numbers of sutures or staples to close the incision and 5 to 10 wire hooks to keep the severed sternum together. Furthermore, such procedures leave an unattractive scar and are painful to the patient. Most patients are out of work for a long period after such an operation and have restricted movement for several weeks. Such surgery often carries additional complications such as instability of the sternum, post-operative bleeding and mediastinal infection. Above all, open procedures are associated with long recuperation times.

Due to the risks attendant to such procedures, there has been a need to develop procedures which minimize invasion of the patient's body tissue and resulting trauma. In this regard, limited open chest techniques have been developed in which the coronary bypass is carried out using an abdominal (subxyphoid) approach or, alternatively, a "Chamberlain" incision (an approximately 8 cm incision at the sternocostal junction), thereby lessening the operating area and the associated complication rate. While the risks attendant to such procedures are generally lower than their open chest counterparts, there is still a need for a minimally invasive surgical technique. Nevertheless, each of these techniques is thoracotomic, requiring an incision to be made in the chest wall through which conventional surgical instruments are introduced to perform conventional coronary bypass surgery.

In order to reduce the risk of patient mortality, infection, and other complications associated with surgical techniques, it is advantageous and desirable to utilize endoscopic and thoracoscopic surgical techniques. Such procedures usually involve the use of surgical trocars to puncture the abdomen or chest, thereby facilitating access to a body cavity through the cannula and a relatively small opening in the patient's body. Typically, such trocars have a diameter of about 3 mm to 15 mm. Surgical instruments and other devices such as fiber optic cameras can be inserted into the body cavity through the cannula. Advantageously, the use of trocars minimizes the trauma associated with many surgical procedures.

Another application involves the implantation and/or attachment of synthetic vascular grafts. Tubular vascular grafts comprising polytetrafluoroethylene (PTFE), Dacron, or other fabric materials may be implanted in a vessel to span a diseased or damaged site. In this application, the diseased portion of the vessel is merely isolated by directing blood flow through the graft. This may be accomplished by attaching the proximal end and distal end of the graft to the vessel wall proximally and distally of the diseased site. In some circumstances, portions of the graft in between the proximal and distal ends are preferably also attached to the vessel wall, to maintain patency throughout the graft. One application of such grafts is to treat abdominal aortic aneurysms, by implanting either a straight segment graft or a Y shaped "bifurcation" graft at the bifurcation of the lower abdominal aorta and the left and right iliac arteries.

When vascular anastomoses are performed, the goal is to achieve a sufficiently leak-proof connection between tubular structures. Typically, such connections in a CABG procedure are established using suturing techniques. Suturing of vascular structures, however, is a tedious and time consuming process. Furthermore, current suturing techniques are not possible using transluminal access, and are not readily adapted for endoscopic use, where the surgeon's freedom of access and movement are limited. Thus, there is a need for an alternative to current suturing techniques that would expedite the anastomosis procedure, and that can be readily adapted for transluminal or endoscopic use.

Various stapling techniques are also known for providing anastomotic connections between organs, such as in intestinal and colorectal anastomosis. Due to the size of these devices, however, they are not easily adapted for use with vascular organs in general, and particularly not for transluminal or endoscopic techniques.

Surgical clips have also been developed, which are intended to facilitate the anastomosis of vascular structures. In this technique, the vascular tissues are approximated, partially everted, and then clipped by applying the arms of the surgical clip over the everted tissue and securing the clip so as to hold the tissue together without penetrating the interior wall of the vessel. Nevertheless, in order to properly utilize these clips, the tissues should be everted. A transluminal approach is thus not readily possible using this technique.

Thus, notwithstanding the various efforts in the prior art, there remains a need for methods and devices for performing vascular anastomoses which minimize the risk of infection, trauma, and other complications associated with conventional surgery, and, in particular, which can be utilized transluminally or in conjunction with an endoscopic technique for vascular anastomosis.

SUMMARY OF THE INVENTION

There is provided in accordance with one aspect of the present invention, a method of attaching a tubular graft to a vessel wall. The method comprises the steps of positioning a tubular graft within a vessel, and positioning a tissue anchor deployment catheter at a first position within the graft, the deployment catheter comprising a first plurality of tissue anchors. The anchors are thereafter advanced into the vessel wall, to secure the graft to the vessel wall. In one embodiment, the advancing the anchors step comprises advancing the anchors through the graft and into the vessel wall. Preferably, the advancing the anchors step comprises advancing at least four anchors into the vessel wall. In one embodiment, the positioning a graft step comprises positioning a tubular PTFE graft. Preferably, the method further comprises the step of advancing a catheter to a second position within the graft, and advancing a second plurality of anchors into the vessel wall. This may be accomplished using a second plurality of anchors, carried by the catheter.

In accordance with another aspect of the present invention, there is provided a method of attaching a first tubular structure to a second tubular structure in a patient. The method comprises the steps of identifying a first tubular structure in the patient, and positioning a second tubular structure in communication with the first tubular structure. An anchor deployment catheter is positioned within at least one of the first and second tubular structures. A plurality of tissue anchors are deployed from the catheter and through at least one of the first and second tubular structures, to attach the first tubular structure to the second tubular structure. The first tubular structure may be an artery or a vein, and the second tubular structure may be a graft. The graft may be autologous vessel tissue, a homograft, a xenograft, or a prosthetic tubular graft.

In accordance with a further aspect of the present invention, there is provided an anastomosis catheter. The anastomosis catheter comprises an elongate flexible body, having a proximal end and distal end. At least one tissue anchor support is provided on the body, moveable between an axial orientation and an inclined orientation. An anchor is movably carried by the anchor support. The anchor comprises a body, having at least one proximal engagement surface for resisting distal travel of the body through the tissue and at least one distal engagement surface for resisting proximal travel of the body through tissue.

In one embodiment, the tissue anchor support comprises a tube. The tube comprises a proximal section, a distal section and a hinge in-between the proximal section and the distal section. An actuator is preferably connected to the distal section, so that proximal retraction of the actuator with respect to the catheter body advances the anchor support from the axial position to the inclined position. Preferably, the catheter further comprises an introducer removably connected to the anchor for driving the anchor into the tissue. Preferably, the catheter comprises from about four anchor supports to about eight anchor supports.

In accordance with another aspect of the present invention, there is provided a method of tacking a tubular graft to a vessel wall. The method comprises the steps of identifying a tubular graft which has been previously positioned within a vessel. A tissue anchor deployment catheter is positioned within the graft, the deployment catheter comprising at least one tissue anchor. The anchor is thereafter advanced into the vessel wall, to secure the graft to the vessel wall.

Further features and advantages of the present invention will become apparent to those of skill in the art in view of the detailed description of preferred embodiments which follows, when considered together with the attached drawings and claims.

BRIEF DESCRIPTION OF THE DRAWINGS

FIGS. 15A-15G are alternate tissue anchors for use with the closure catheter of the present invention.

FIG. 16 is a perspective view of a buckling rivet type anchor in accordance with the present invention.

FIG. 17 is a perspective view of the buckling rivet of FIG. 16, carried by an introducer.

FIG. 18 is a cross-sectional schematic view of a buckling rivet of the type shown in FIG. 16, deployed on a tissue membrane.

DETAILED DESCRIPTION OF THE PREFERRED EMBODIMENT

For simplicity, the present invention will be described primarily in the context of a left atrial appendage closure procedure, and as modified for use in tissue-to-tissue or synthetic graft-to-tissue anastomosis. As used herein the term "anastomosis" shall include securing a tubular synthetic graft within a vessel, such as to span an aneurysm, as well as the end to end and end to side orientation discussed in the Background of the Invention. However, the device and methods herein are readily applicable to a wider variety of closure or attachment procedures, and all such applications are contemplated by the present inventors. For example, additional heart muscle procedures such as atrial septal defect closure and patent ductus arteriosis closure are contemplated. Vascular procedures such as isolation or repair of aneurysms, anastomosis of vessel to vessel or vessel to prosthetic tubular graft (e.g., PTFE or Dacron tubes, with or without wire support structures as are well known in the art) joints may also be accomplished using the devices of the present invention. Attachment of implantable prostheses, such as attachment of the annulus of a prosthetic tissue or mechanical heart valve may be accomplished. A variety of other tissue openings, lumens, hollow organs and surgically created passageways may be closed, patched or reduced in volume in accordance with the present invention. For example, an opening in a tissue plane may be closed or patched, such as by attaching a fabric or tissue sheet across the opening. In one specific application, the device of the present invention is used to anchor a fabric patch to close an atrial septal defect. The target aperture or cavity may be accessed transluminally (e.g., vascular catheter or endoscope) or through solid tissue, such as transmural, percutaneous or other approach. The present invention may also be used in an open surgical procedure such as to close the left atrial appendage during open heart surgery to correct or address a different condition. In another example, the device is advanced through the percutaneous opening and used to close a vascular puncture such as a femoral artery access site for a PTA or other diagnostic or therapeutic interventional procedure. Adaptation of the devices and methods disclosed herein to accomplish procedures such as the foregoing will be apparent to those of skill in the art in view of the disclosure herein.

Figure 1:
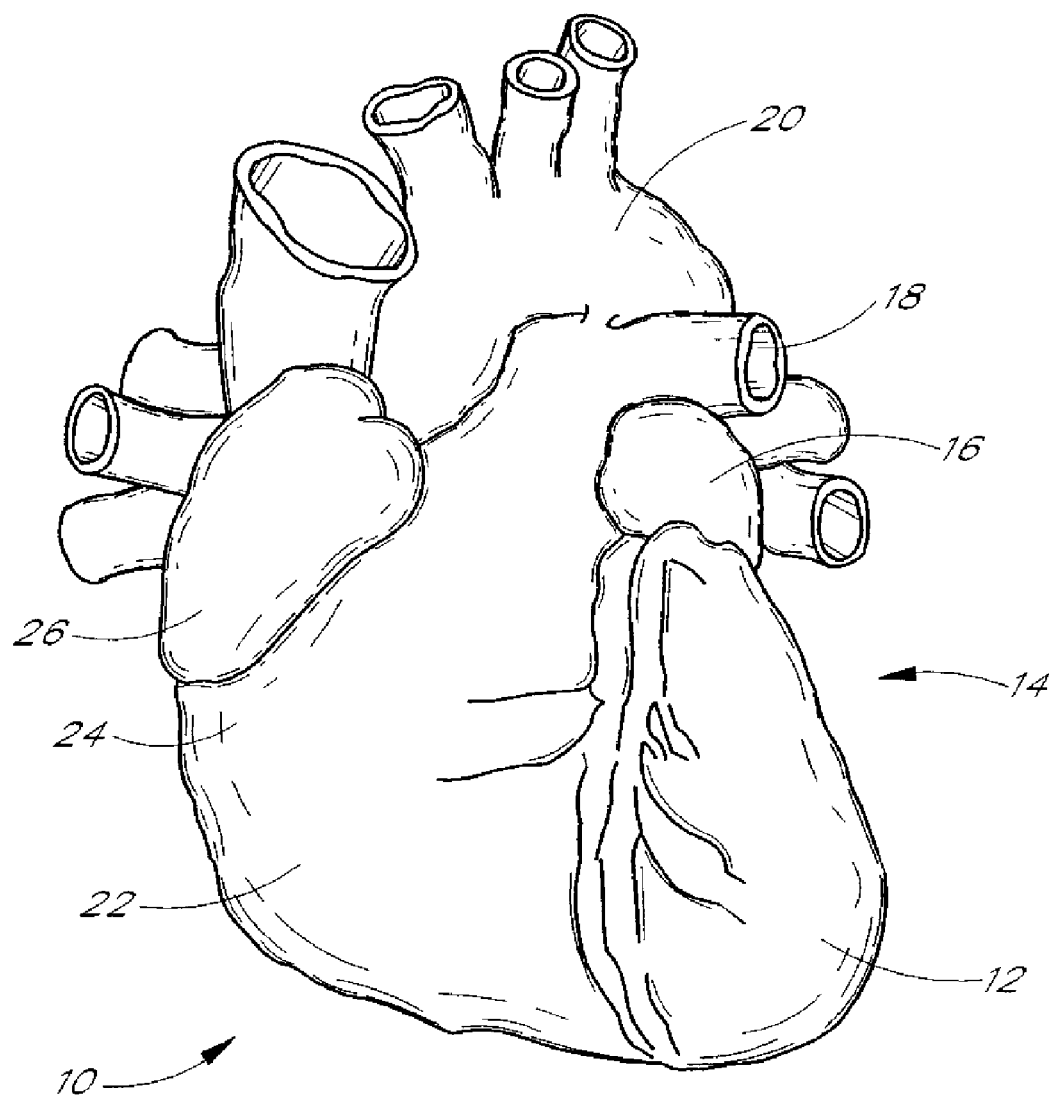
FIG. 1 is an anterior illustration of a heart, with the proximal parts of the great vessels.

Referring to FIG. 1, a heart 10 is illustrated to show certain portions including the left ventricle 12, the left atrium 14, the left atrial appendage (LAA) 16, the pulmonary artery 18, the aorta 20, the right ventricle 22, the right atria 24, and the right atrial appendage 26. As is understood in the art, the left atrium 14 is located above the left ventricle 12 and the two are separated by the mitral valve (not illustrated). The LAA 16 is normally in fluid communication with the left atrium 14 such that blood flows in and out of the LAA 16 as the heart 10 beats.

In accordance with the present invention, a closure catheter 38 is advanced through the heart and into the LAA. In general, the closure catheter 38 is adapted to grasp tissue surrounding the opening to the LAA, and retract it radially inwardly to reduce the volume of and/or close the LAA. The LAA is thereafter secured in its closed orientation, and the closure catheter 38 is removed. Specific aspects of one embodiment of the closure catheter in accordance with the present invention are described in greater detail below.

The LAA may be accessed through any of a variety of pathways as will be apparent to those of skill in the art. Transeptal access, as contemplated by FIG. 2, may be achieved by introducing a transeptal catheter through the femoral or jugular vein, and transluminally advancing the catheter into the right atrium. Once in the right atrium, a long hollow needle with a preformed curve and a sharpened distal tip is forcibly inserted through the fossa ovalis. A radiopaque contrast media may then be injected through the needle to allow visualization and ensure placement of the needle in the left atrium, as opposed to being in the pericardial space, aorta, or other undesired location.

Once the position of the needle in the left atrium is confirmed, the transeptal catheter is advanced into the left atrium. The closure catheter 38 may then be advanced through the transeptal catheter 30, and steered or directed into the left atrial appendage. Alternative approaches include venous transatrial approaches such as transvascular advancement through the aorta and the mitral valve. In addition, the devices of the present invention can be readily adapted for use in an open heart surgical procedure, although transluminal access is presently preferred.

Figure 2:
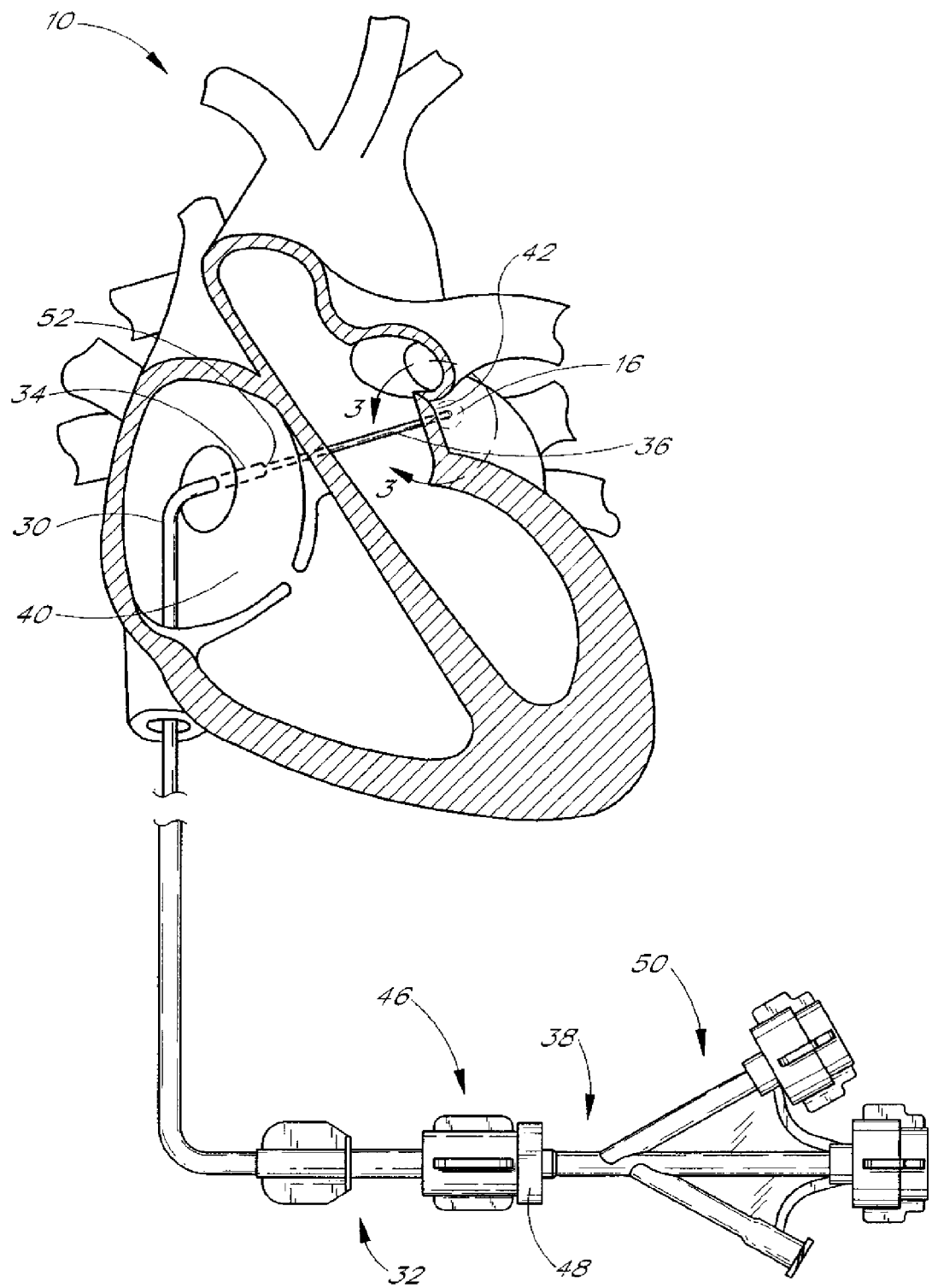
FIG. 2 is a schematic cross section through the heart with a transeptal catheter deployed through the septum and a closure catheter extending into the LAA.

Thus, referring to FIG. 2, a transeptal catheter 30 has a proximal end 32 and a distal end 34. The distal end 34 of the transeptal catheter 30 has breached the septum 40 of the patient's heart 10 and is disposed adjacent the opening 42 of the patient's LAA 16. The distal end 36 of a closure catheter 38 extends from the distal end 34 of the transeptal catheter 30 and into the LAA 16.

At the proximal end 46 of the transeptal catheter 30, a luer connector coupled to a hemostasis valve 48 prevents the egress of blood from a central lumen of the transeptal catheter 30. The proximal end 50 of the closure catheter 38 extends proximally from the hemostasis valve 48. Additional details concerning the use and design of transeptal access catheters are well known in the art and will not be discussed further herein.

Figure 3A:
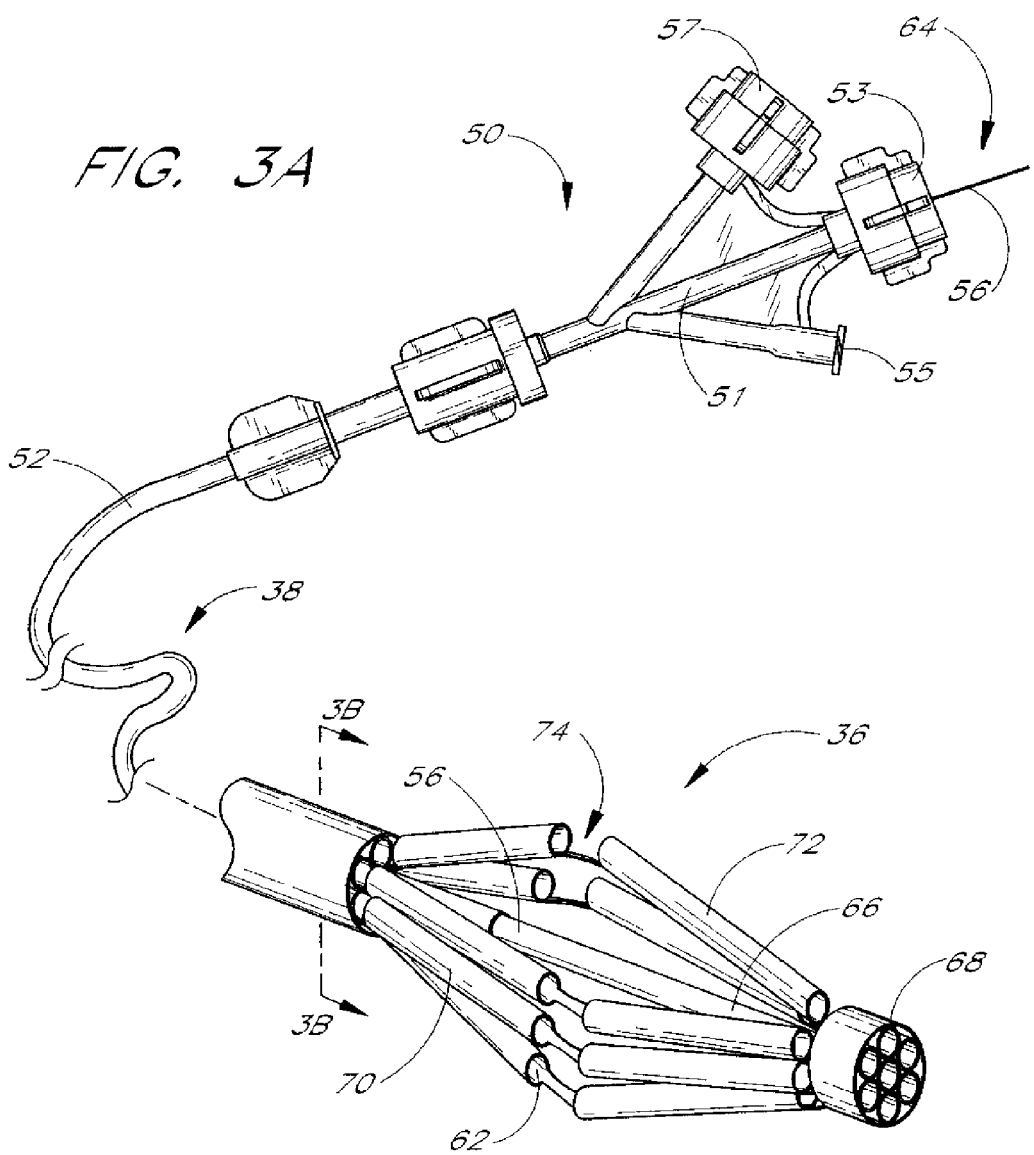
FIG. 3A is an enlarged perspective view of the distal end of a closure catheter in accordance with the present invention.
Figure 3B:
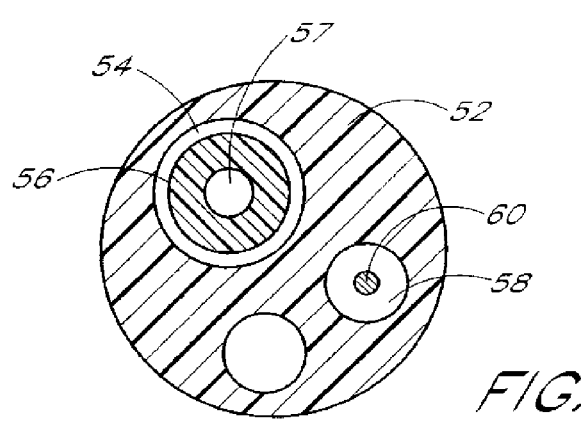
FIG. 3B is a cross section taken along the lines 3B-3B of FIG. 3A.

Referring to FIGS. 2 and 3, the closure catheter 38 thus has a proximal end 50, a distal end 36, and an elongate flexible tubular body 52 extending therebetween. The axial length of the closure catheter 38 can be varied, depending upon the intended access point and pathway. For a femoral vein-transeptal approach, the closure catheter 38 generally has an axial length within the range of from about 100 cm to about 140 cm, and, in one embodiment, about 117 cm.

The outside diameter of the flexible body 52 can also be varied, depending upon the number of internal lumen and other functionalities as will be understood by those of skill in the art. In one embodiment, the outside diameter is about 12 FR (0.156 inches), and closure catheters are contemplated to have OD's generally within the range of from about 0.078 inches to about 0.250 inches. Diameters outside of the above range may also be used, provided that the functional consequences of the diameter are acceptable for the intended application of the catheter.

For example, the lower limit of the outside diameter for tubular body 52 in a given application will be a function of the number of fluid or other functional lumen contained within the catheter. In addition, tubular body 52 must have sufficient pushability to permit the catheter to be advanced to its target location within the heart without buckling or undesirable bending. The ability of the tubular body 52 to transmit torque may also be desirable, such as in embodiments in which the tissue anchor deployment guides are not uniformly circumferentially distributed about the distal end 36 of the catheter. Optimization of the outside diameter of the catheter, taking into account the flexibility, pushability and torque transmission characteristics can be accomplished through routine experimentation using conventional catheter design techniques well known to those of skill in the art.

The flexible body 52 can be manufactured in accordance with any of a variety of known techniques. In one embodiment, the flexible body 52 is extruded from any of a variety of materials such as HDPE, Pebax, nylon, polyimide, and PEEK. Alternatively, at least a portion or all of the length of tubular body 52 may comprise a spring coil, solid walled hypodermic needle or other metal tubing, or braided reinforced wall, as are known in the art.

The proximal end 50 of the closure catheter 38 is provided with a manifold 51, having a plurality of access ports. Generally, manifold 51 is provided with an access port 53 which may be used as a guidewire port in an over the wire embodiment, and a deployment wire port 57. Additional access ports such as a contrast media introduction port 55, or others may be provided as needed, depending upon the functional requirements of the catheter.

The tubular body 52 has at least a first actuator lumen 54, for axially movably receiving an actuator 56. Actuator 56 extends between a proximal end 64 at about the proximal end of the closure catheter, and a distal end 66 at or near the distal end 36 of the closure catheter 38. The distal end 66 of the actuator 56 is secured to a cap 68. In the illustrated embodiment, the actuator lumen 54 is in communication with the access port 53 to permit the actuator 56 to extend proximally therethrough.

Actuator 56 can have a variety of forms, depending upon the construction of the anchor supports 62 on the distal end 36 of the closure catheter 38. In general, the catheter in the area of the anchor supports 62 should have a crossing profile of no more than about 14 French for transluminal advancement and positioning. However, the anchor supports must then be capable of directing tissue anchors into the wall of the cavity or lumen which may have an inside diameter on the order of about 1.5 cm to about 3 cm in the case of the LAA in an average adult. The device of the present invention can be readily scaled up or down depending upon the intended use, such as to accommodate a 5 cm to 10 cm cavity in GI tract applications or 5 mm to about 2 cm for vascular applications. For this purpose, the anchor supports are preferably moveable between a reduced cross sectional orientation and an enlarged cross sectional orientation to aim at, and, in some embodiments, contact the target tissue surface.

One convenient construction to accomplish the foregoing is for each anchor support 62 to take the form of a lever arm structure which is pivotably connected at one end to the catheter body. This construction permits inclination of the anchor support throughout a continuous range of outside diameters which may be desirable to aim the anchor and accommodate different treatment sites and/or normal anatomical variation within the patient population.

A laterally moveable anchor support can be moved between an axial orientation and an inclined orientation in a variety of ways. One convenient way is through the use of a pull wire or other actuator which increases the diameter of the deployment zone of the catheter in response to an axial shortening of fixed length moveable segments as disclosed in more detail below. For this construction, the actuator will be under pulling tension during actuation. Any of a variety of structures such as polymeric or metal single or multiple strand wires, ribbons or tubes can be used. In the illustrated embodiment, the actuator 56 comprises stainless steel tube, having an outside diameter of about 0.025 inches.

A pull wire can alternatively be connected to the radially outwardly facing surface and preferably near the distal end of each anchor support, and each anchor support is hingably attached at its proximal end to the catheter. Proximal traction on the pull wire will cause the anchor support to incline radially outwardly in the distal direction, and toward the target tissue.

In an alternate construction, the anchor support is inclined under a compressive force on the actuator 56. For example, the embodiment described in detail below can readily be converted to a push actuated system by axially immovable fixing the distal end of the anchor guide assembly to the catheter and slideably pushing the proximal end of the anchor guide assembly in the distal direction to achieve axial compression as will become apparent from the discussion below.

Push wire actuators have different requirements, than pull actuator systems, such as the ability to propagate a sufficient compressive force without excessive compression bending or friction. Thus, solid core wires or tubular structures may be preferred, as well as larger outside diameters compared to the minimum requirements in a pull actuated system. Thus, the inside diameter of the actuator lumen 57 may be varied, depending upon the actuator system design. In the illustrated embodiment, the actuator lumen 57 has an ID of about 0.038 inches, to slideably accommodate the 0.025 inch OD actuator 56.

A radially outwardly directed force on the anchor supports 62 can be provided by any of a variety of alternative expansion structures, depending upon desired performance and construction issues. For example, an inflatable balloon can be positioned radially inwardly from a plurality of hingably mounted anchor supports 62, and placed in communication with actuator lumen 54 which may be used as an inflation lumen. Any of a variety of balloon materials may be used, ranging in physical properties from latex for a highly compliant, low pressure system to PET for a noncompliant high pressure and consequently high radial force system, as is understood in the balloon angioplasty arts.

The tubular body 52 may additionally be provided with a guidewire lumen 57, or a guidewire lumen 57 may extend coaxially throughout the length of a tubular actuator 56 as in the illustrated embodiment.

The tubular body 52 may additionally be provided with a deployment lumen 58, for axially movably receiving one or more deployment elements 60 such as a wire, or suture for deploying one or more tissue anchors 90 into the target tissue 110. Deployment force for deploying the tissue anchors 90 can be designed to be in either the distal or proximal direction, and many of the considerations discussed above in connection with the actuator 56 and corresponding actuator lumen 54 apply to the deployment system as well. In the illustrated embodiment, deployment of the tissue anchors 90 is accomplished by proximal retraction on the deployment element 60 which, in turn, retracts deployment wire 106. Pushability is thus not an issue, and common suture such as 0.008 inch diameter nylon line may be used. For this embodiment, deployment lumen 58 has an inside diameter of about 0.038 inches. The deployment lumen 58 can be sized to receive either a single deployment element 60, or a plurality of deployment elements 106 such as a unique suture for each tissue anchor.

The distal end 36 of the closure catheter 38 is provided with one or more anchor supports 62, for removably carrying one or more tissue anchors. Preferably, two or more anchor supports 62 are provided, and, generally, in a device intended for LAA closure, from about 3 to about 12 anchor supports 62 are provided. In the illustrated embodiment, six anchor supports 62 are evenly circumferentially spaced around the longitudinal axis of the closure catheter 38.

Each anchor support 62 comprises a surface 63 for slideably retaining at least one tissue anchor, and permitting the tissue anchor to be aimed by manipulation of a control on the proximal end 50 of the closure catheter 38. Specific details of one embodiment of the anchor support 62 having a single anchor therein will be discussed below. Multiple anchors, such as two or three or more, can also be carried by each anchor support for sequential deployment.

The anchor supports 62 are movable between an axial orientation and an inclined orientation, in response to manipulation of a proximal control. The proximal control can take any of a variety of forms, such as slider switches or levers, rotatable levers or knobs, or the like, depending upon the desired performance. For example, a rotatable knob control can permit precise control over the degree of inclination of the anchor supports 62. A direct axial slider control, such as a knob or other grip directly mounted to the actuator 56 will optimize tactile feedback of events such as the anchor supports 62 coming into contact with the target tissue.

Each of the illustrated anchor supports 62 comprises at least a proximal section 70, a distal section 72, and a flex point 74. See FIG. 4. The distal end 73 of each distal section 72 is movably connected to the catheter body or the cap 68. In this embodiment, proximal retraction of the actuator 56 shortens the axial distance between the proximal end 71 of the proximal section 70 and the distal end 73 of distal section 72, forcing the flex point 74 radially outwardly from the longitudinal axis of the closure catheter 38. In this manner, proximal retraction of the actuator 56 through a controlled axial distance will cause a predictable and controlled increase in the angle between the proximal and distal sections 70 and 72 of the anchor support 62 and the longitudinal axis of the catheter. This is ideally suited for aiming a plurality of tissue anchors at the interior wall of a tubular structure, such as a vessel or the left atrial appendage.

Figure 4:
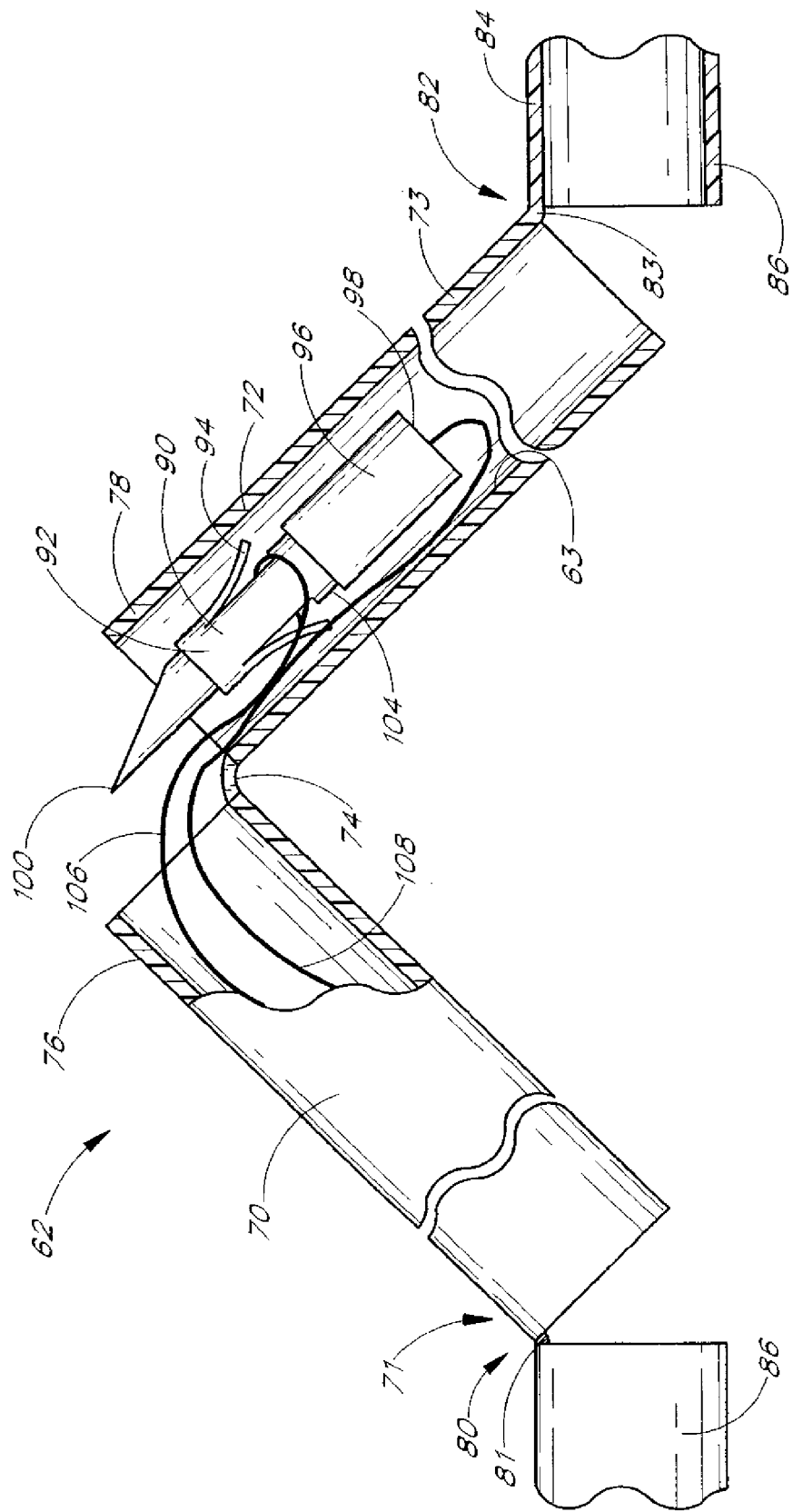
FIG. 4 is a partial cross-sectional view of a tissue anchor and introducer, positioned within an anchor guide in accordance with the present invention.
Figure 5:
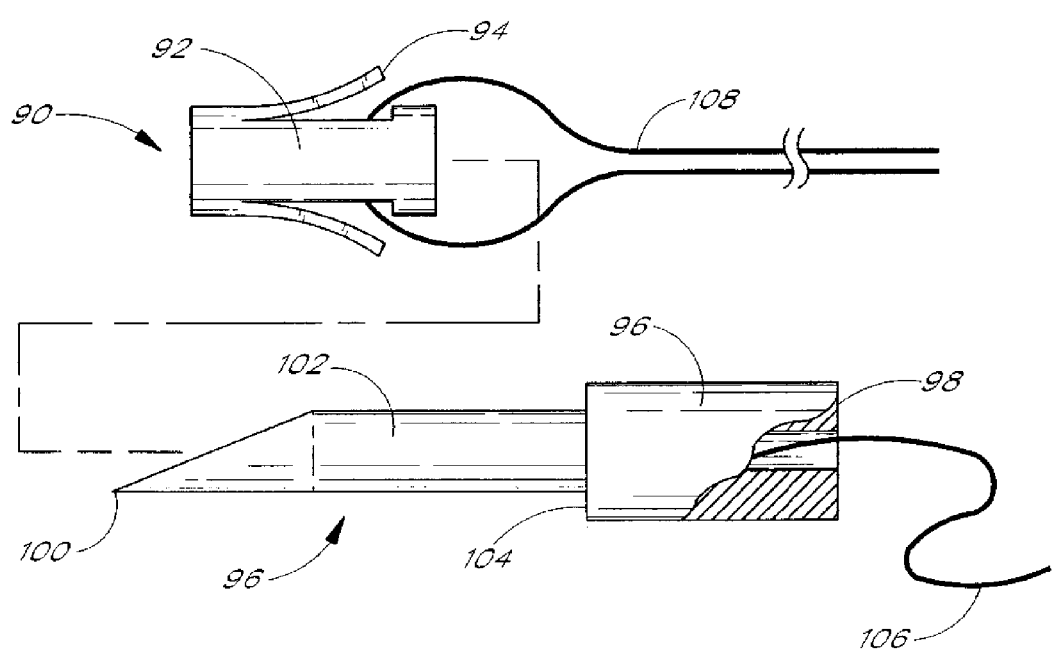
FIG. 5 is an exploded view of a tissue anchor and introducer in accordance with one aspect of the invention.

Referring to FIG. 4, there is illustrated an enlarged detailed view of one anchor support 62 in accordance with the present invention. The proximal section 70 and distal section 72 preferably comprise a tubular wall 76 and 78 joined at the flex point 74. In one embodiment, the proximal section 70 and distal section 72 may be formed from a single length of tubing, such as by laser cutting, photolithography, or grinding to separate the proximal section 70 from the distal section 72 while leaving one or two or more integrally formed hinges at flex point 74. Any of a variety of polymeric or metal tubing may be utilized for this purpose, including stainless steel, Nitinol or other super-elastic alloys, polyimide, or others which will be appreciated by those of skill in the art in view of the disclosure herein.

In the illustrated six tube embodiment, the proximal section 70 and distal section 72 are formed from a length of PEEK tubing having an inside diameter of about 0.038 inches, an outside diameter of about 0.045 inches and an overall length of about 1.4 inches. In general, if more than six anchor supports 62 are used, the diameter of each will be commensurately less than in the six tube embodiment for any particular application. When the proximal section 70 and the distal section 72 are coaxially aligned, a gap having an axial length of about 0.030 is provided therebetween. In the illustrated embodiment, the proximal section 70 and distal section 72 are approximately equal in length although dissimilar lengths may be desirable in certain embodiments. The length of the portion of the anchor support 62 which carries the tissue anchor 90 is preferably selected for a particular procedure or anatomy so that the anchor support 62 will be inclined at an acceptable launch angle when the deployment end of the anchor support 62 is brought into contact with the target tissue 110. Lengths from the hinge to the deployment end of the anchor support 62 within the range of from about 0.5 cm to about 1.5 cm are contemplated for the LAA application disclosed herein.

For certain applications, the proximal section 70 is at least about 10% and preferably at least about 20% longer than the distal section 72. For example, in one device adapted for the LAA closure application, the proximal section 70 in a six anchor device has a length of about 0.54 inches, and the distal section 72 has a length of about 0.40 inches. Each anchor support has an OD of about 0.045 inches. As with previous embodiments, the functional roles and/or the dimensions of the proximal and distal sections can be reversed and remain within the scope of the present invention. Optimization of the relative lever arm lengths can be determined for each application taking into account a variety of variables such as desired device diameter, target lumen or tissue aperture diameter, launch angle and desired pull forces for aiming and deployment.

The proximal end 71 of the proximal section 70 and distal end 73 of distal section 72 are movably secured to the closure catheter 38 in any of a variety of ways which will be apparent to those of skill in the art in view of the disclosure herein. In the illustrated embodiment, each anchor support 62 comprises a four segment component which may be constructed from a single length of tubing by providing an intermediate flex point 74, a proximal flex point 80 and a distal flex point 82. Distal flex point 82 provides a pivotable connection between the anchor support 62 and a distal connection segment 84. The distal connection segment 84 may be secured to the distal end of actuator 56 by any of a variety of techniques, such as soldering, adhesives, mechanical interfit or others, as will be apparent to those of skill in the art. In the illustrated embodiment, the distal connection segment 84 is secured to the distal end 66 of the actuator 56 by adhesive bonding.

The proximal flex point 80 in the illustrated embodiment separates the proximal section 70 from a proximal connection segment 86, which is attached to the catheter body 52. In this construction, proximal axial retraction of the actuator 56 with respect to the tubular body 52 will cause the distal connection segment 84 to advance proximally towards the proximal connection segment 86, thereby laterally displacing the flex point 74 away from the longitudinal axis of the closure catheter 38. As a consequence, each of the proximal section 70 and the distal section 72 are aimed at an angle which is inclined outwardly from the axis of the closure catheter 38.

In general, each flex point 80, 82 includes a hinge 81, 83 which may be, as illustrated, a strip of flexible material. The hinges 81 and 83 are preferably positioned on the inside radius of the flex points 80, 82, respectively, for many construction materials. For certain materials, such as Nitinol or other superelastic alloys, the hinges 81 and 83 can be positioned at approximately 90.degree. or 180.degree. or other angle around the circumference of the tubular anchor guide from the inside radius of the flex point.

A tissue anchor 90 is illustrated as positioned within the distal section 72, for deployment in a generally proximal direction. Alternatively, the anchor 90 can be loaded in the proximal section 70, for distal deployment. A variety of tissue anchors can be readily adapted for use with the closure catheter 38 of the present invention, as will be appreciated by those of skill in the art in view of the disclosure herein. In the illustrated embodiment, the tissue anchor 90 comprises a tubular structure having a body 92, and one or more barbs 94. Tubular body 92 is coaxially movably disposed about an introducer 96. Introducer 96 has a proximal section 98, and a sharpened distal tip 100 separated by an elongate distal section 102 for slideably receiving the tissue anchor 90 thereon.

The tissue anchor 90 in the illustrated embodiment comprises a tubular body 92 having an axial length of about 0.118 inches, an inside diameter of about 0.017 inches and an outside diameter of about 0.023 inches. Two or more barbs 94 may be provided by laser cutting a pattern in the wall of the tube, and bending each barb 94 such that it is biased radially outwardly as illustrated. The tissue anchor 90 may be made from any of a variety of biocompatible metals such as stainless steel, Nitinol, Elgiloy or others known in the art. Polymeric anchors such as HDPE, nylon, PTFE or others may alternatively be used. For embodiments which will rely upon a secondary closure structure such as staples, sutures or clips to retain the LAA or other cavity closed, the anchor may comprise a bioabsorbable or dissolvable material so that it disappears after a period of time. An anchor suture 108 is secured to the anchor.

In one embodiment of the invention, the introducer 96 has an axial length of about 0.250 inches. The proximal section 98 has an outside diameter of about 0.023 inches and an axial length of about 0.100 inches. The distal section 102 has an outside diameter of about 0.016 inches and an axial length of about 0.150 inches. The outside diameter mismatch between the proximal section 98 and the distal section 102 provides a distally facing abutment 104, for supporting the tubular body 92 of tissue anchor 90, during the tissue penetration step. A deployment wire (e.g., a suture) 106 is secured to the proximal end 98 of the introducer 96. The introducer 96 may be made in any of a variety of ways, such as extrusion or machining from stainless steel tube stock.

Figure 6A:
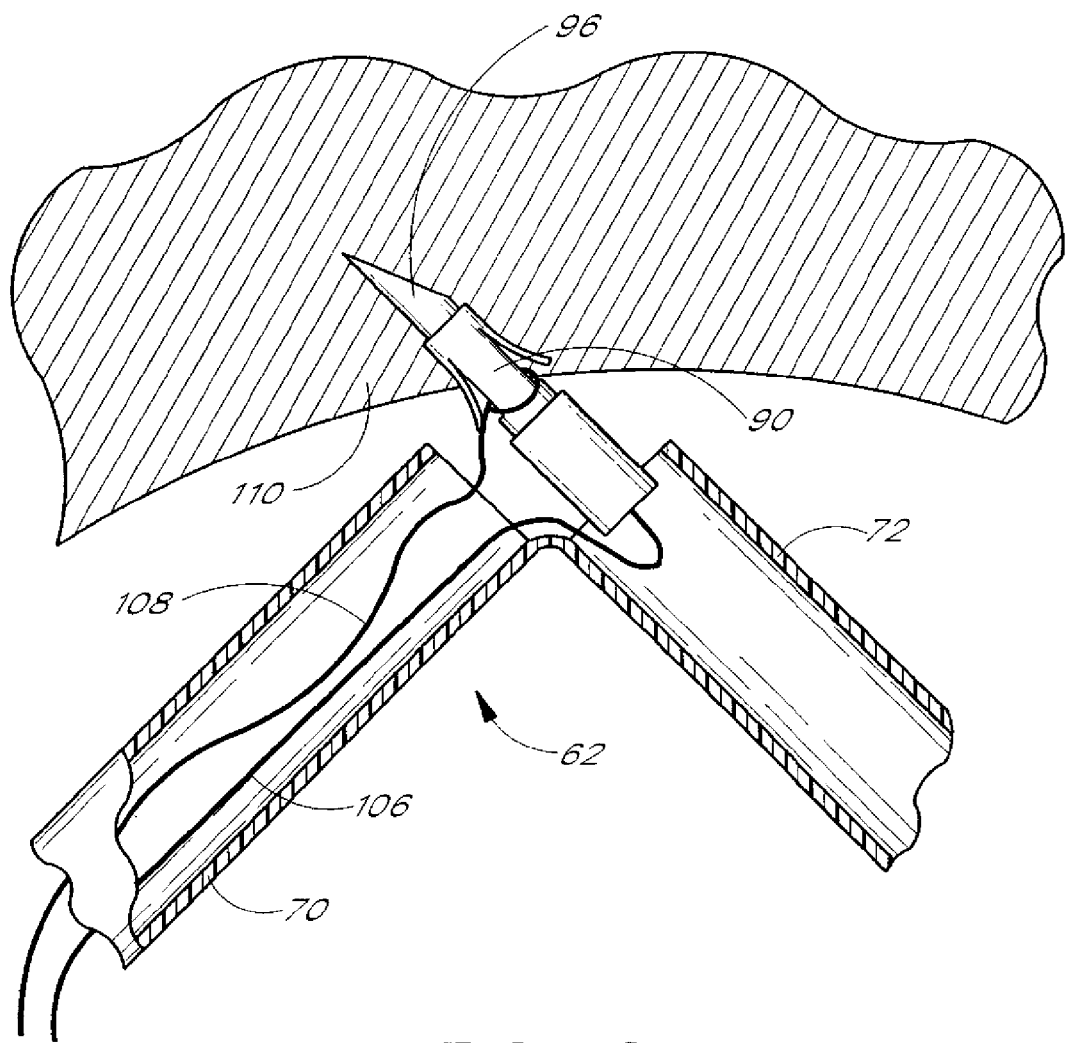
FIG. 6A is a schematic illustration of a tissue anchor and introducer advancing into a tissue surface.
Figure 6B:
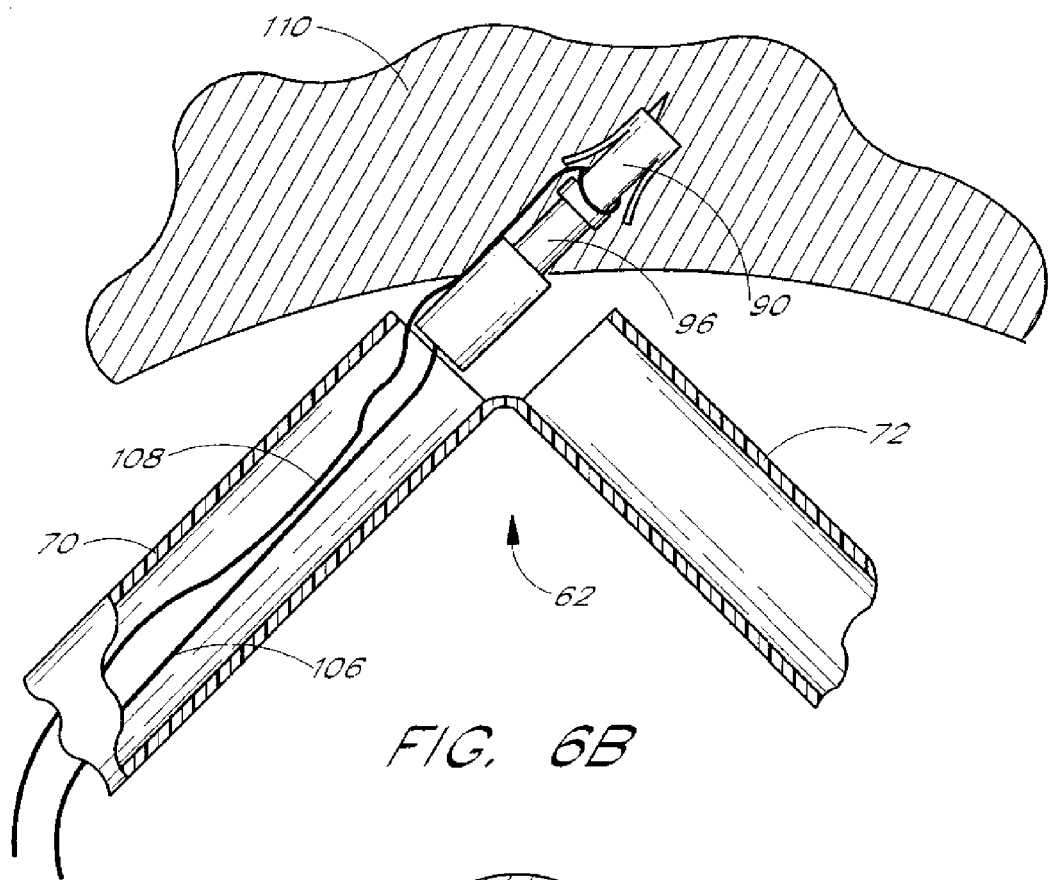
FIG. 6B is an illustration as in FIG. 6A, with the anchor positioned within the tissue and the introducer partially retracted.
Figure 6C:
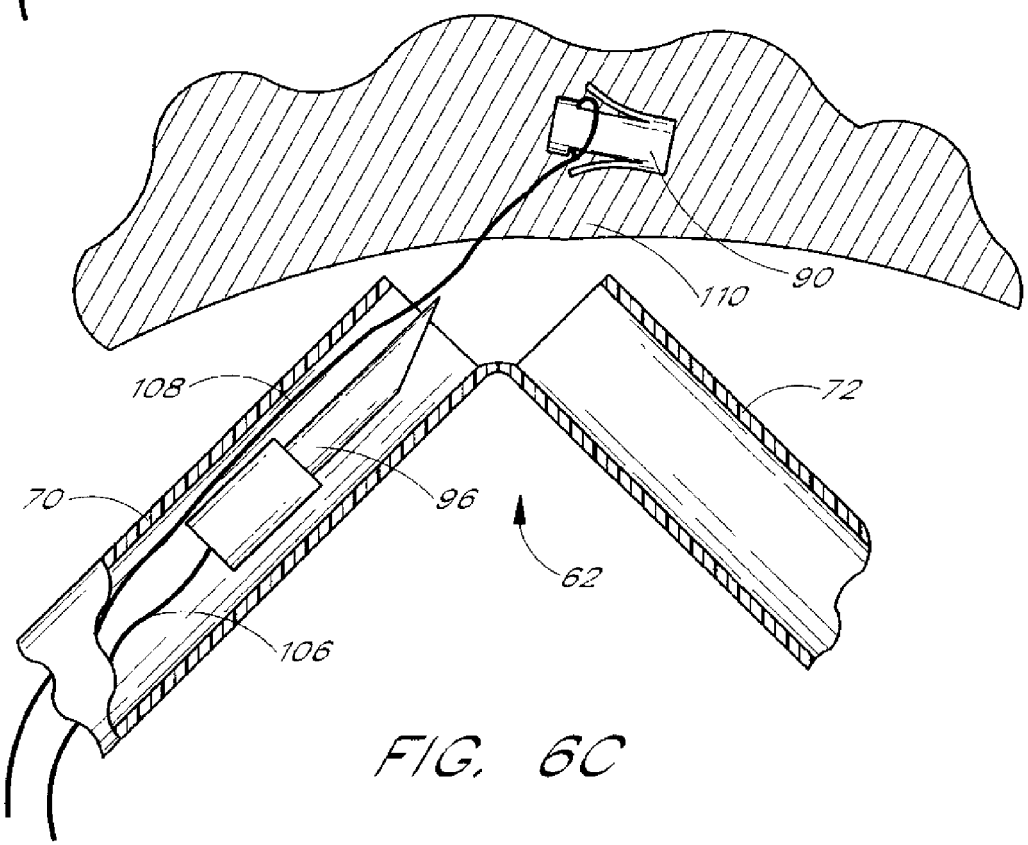
FIG. 6C is an illustration as in FIG. 6B, with the introducer fully retracted and the anchor positioned within the tissue.

Referring to FIGS. 6A-6C, introduction of the tissue anchor 90 into target tissue 110 is illustrated following inclination of the anchor support 62 with respect to the longitudinal axis of the closure catheter 38. Proximal retraction of the deployment wire 106 causes the tissue anchor 90 and introducer 96 assembly to travel axially through the distal section 72, and into the tissue 110. Continued axial traction on the deployment wire 106 causes the longitudinal axis of the introducer 96 to rotate, such that the introducer 96 becomes coaxially aligned with the longitudinal axis of the proximal section 70. Continued proximal traction on the deployment wire 106 retracts the introducer 96 from the tissue anchor 90, leaving the tissue anchor 90 in place within the tissue. The anchor suture 108 remains secured to the tissue anchor 90, as illustrated in FIG. 6C.

Figure 7:
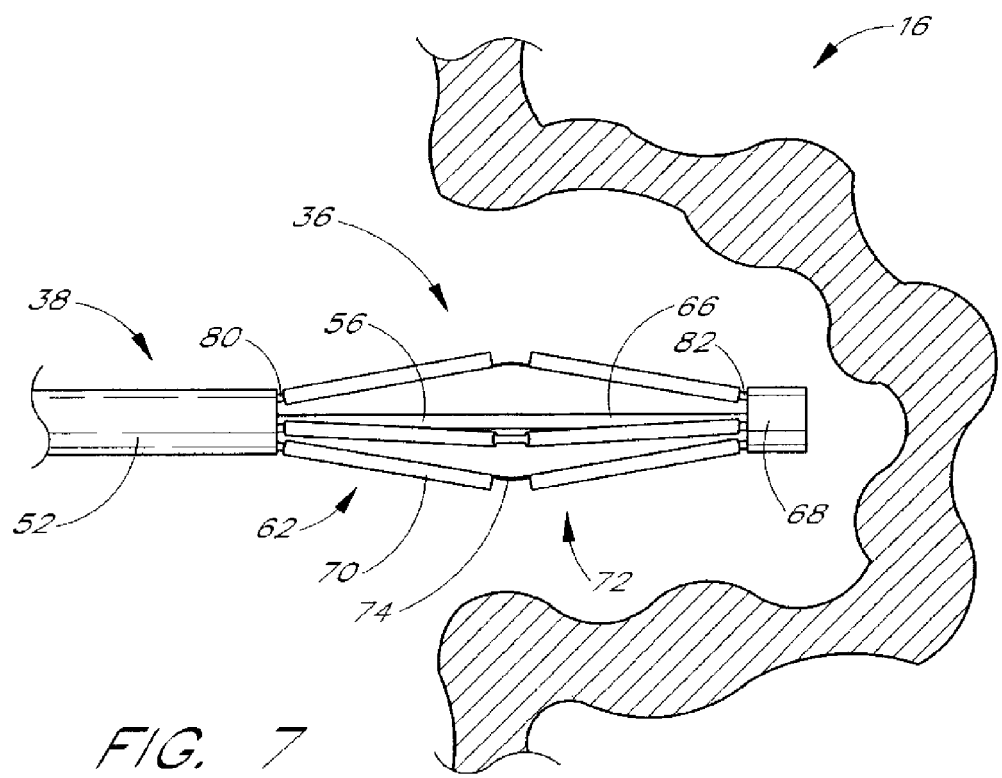
FIG. 7 shows a schematic view of a closure catheter disposed within the opening of the LAA.
Figure 8:
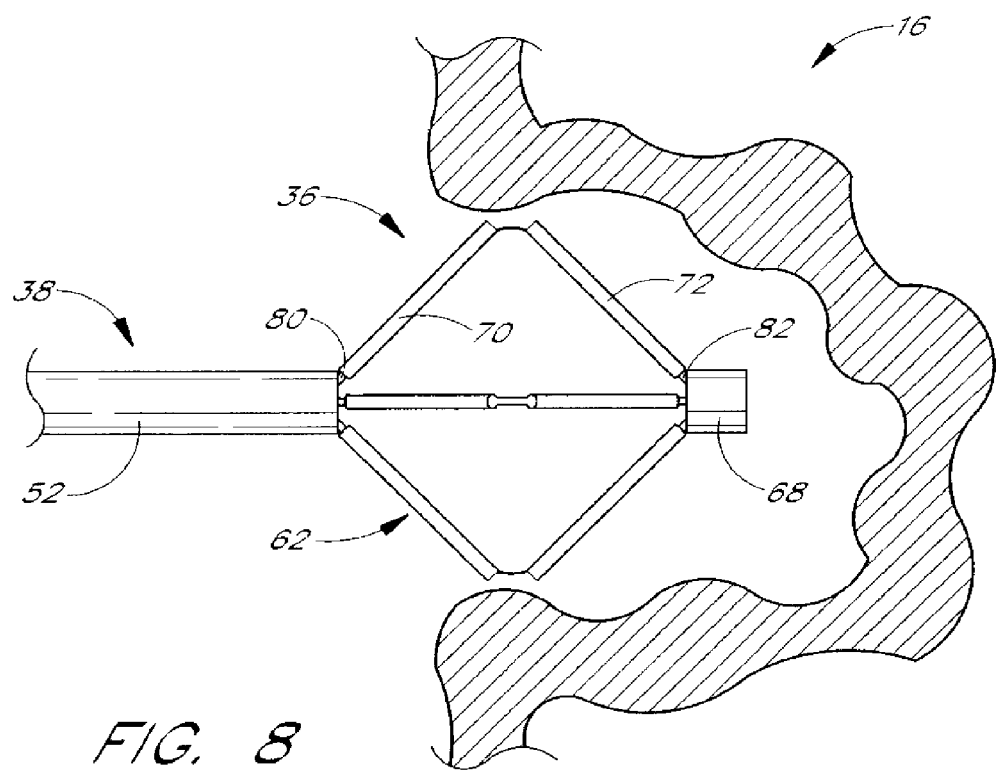
FIG. 8 is a schematic illustration of the opening of the LAA as in FIG. 7, with the anchor guides in an inclined orientation.

In use, the closure catheter 38 is percutaneously introduced into the vascular system and transluminally advanced into the heart and, subsequently, into the left atrial appendage using techniques which are known in the art. Referring to FIG. 7, the distal end 36 of the closure catheter 38 is positioned at about the opening of the LAA 16, and the position may be confirmed using fluoroscopy, echocardiography, or other imaging. The actuator 56 is thereafter proximally retracted, to incline the anchor supports 62 radially outwardly from the longitudinal axis of the closure catheter 38, as illustrated in FIG. 8. Preferably, the axial length of the proximal section 70 of each anchor support 62, in combination with the angular range of motion at the proximal flex point 80, permit the flex point 74 to be brought into contact with the tissue surrounding the opening to the LAA. In general, this is preferably accomplished with the distal section 72 inclined at an angle within a range of from about 45.degree. to about 120.degree. with respect to the longitudinal axis of the closure catheter 38. Actuator 56 may be proximally retracted until the supports 62 are fully inclined, or until tactile feedback reveals that the anchor supports 62 have come into contact with the surrounding tissue 110.

Figure 9:
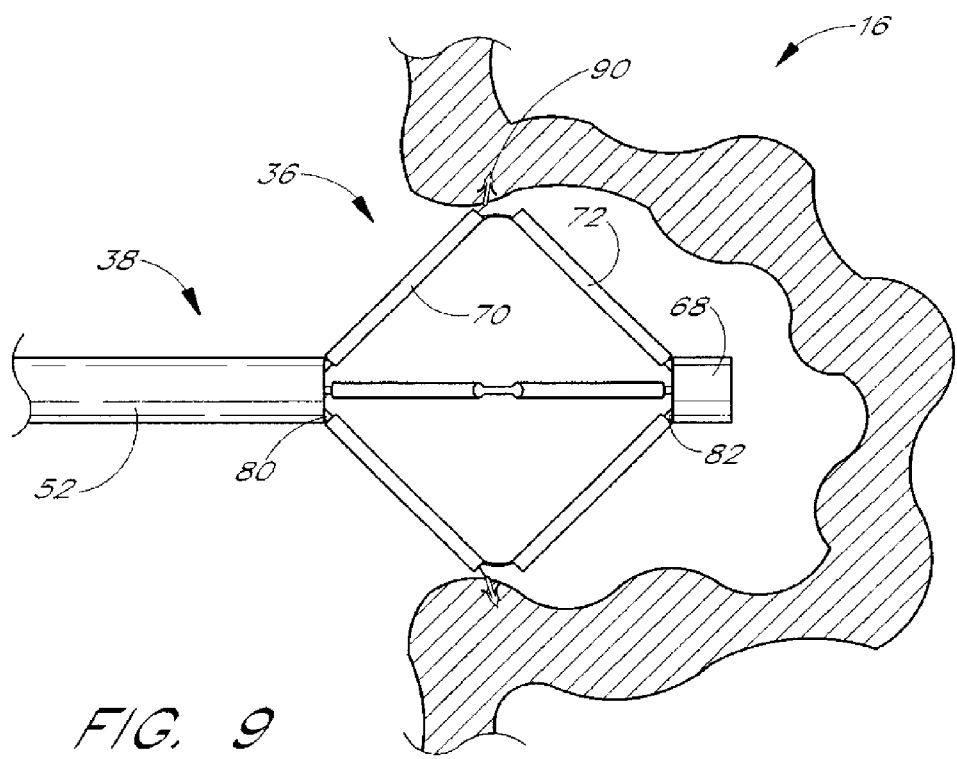
FIG. 9 is a schematic illustration as in FIG. 8, with tissue anchors deployed from the anchor guides.
Figure 10:
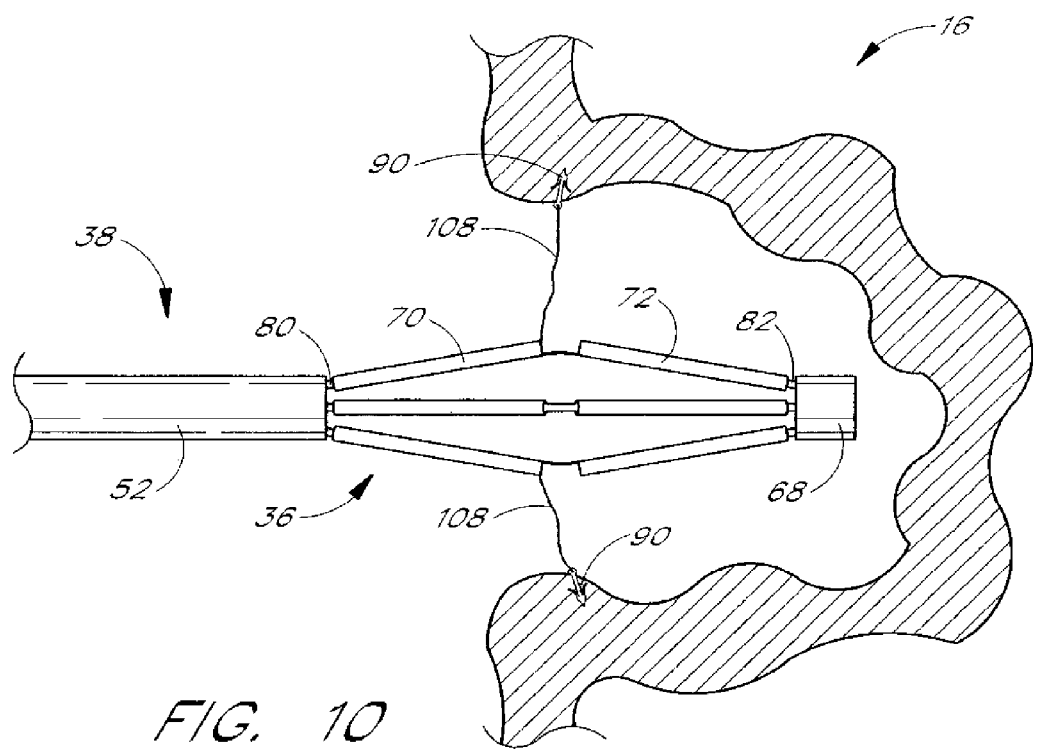
FIG. 10 is a schematic illustration as in FIG. 9, with the anchor guides retracted into an axial orientation.
Figure 11:
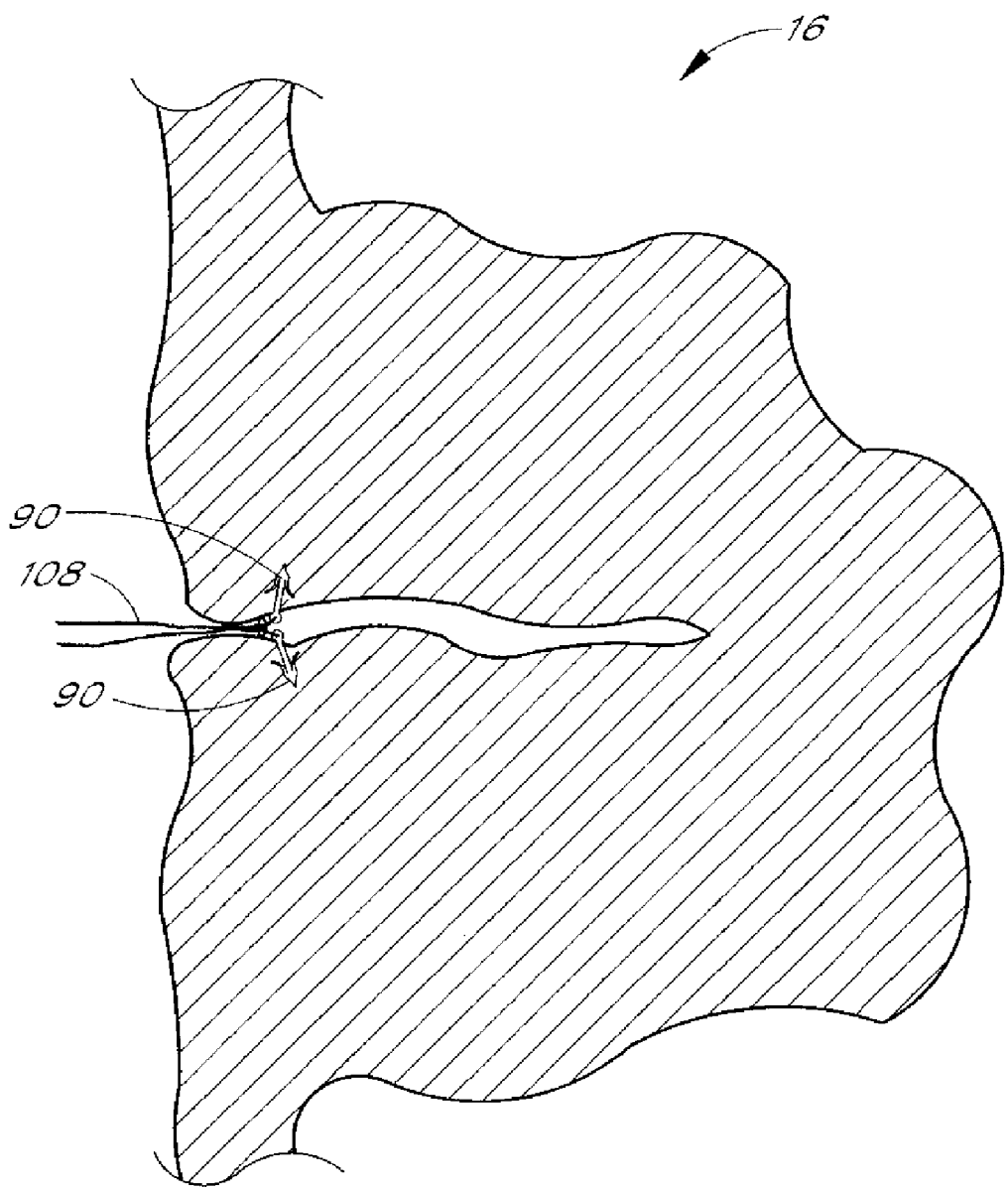
FIG. 11 is a schematic illustration as in FIG. 10, with the closure catheter retracted and the LAA drawn closed using the tissue anchors.

Following inclination of the anchor supports 62, the deployment wire 106 is proximally retracted thereby advancing each of the tissue anchors 90 into the surrounding tissue 110 as has been discussed. See FIG. 9. The anchor supports 62 are thereafter returned to the first, axial position, as illustrated in FIG. 10, for retraction from the left atrial appendage. Proximal retraction on the anchor sutures 108 such as through a tube, loop or aperture will then cause the left atrial appendage wall to collapse as illustrated in FIG. 11. Anchor sutures may thereafter be secured together using any of a variety of conventional means, such as clips, knots, adhesives, or others which will be understood by those of skill in the art. Alternatively, the LAA may be sutured, pinned, stapled or clipped shut, or retained using any of a variety of biocompatible adhesives.

In an alternate embodiment, a single suture is secured to a first anchor and slideably connected to the remainder of the anchors such that proximal retraction of the suture following deployment of the anchors draws the tissue closed in a "purse string" fashion. A similar technique is illustrated in FIGS. 31A and 31B in U.S. Pat. No. 5,865,791 to Whayne, et al, the disclosure of which is incorporated in its entirety herein by reference.

The foregoing closure techniques may be accomplished through the closure catheter, or through the use of a separate catheter. The closure catheter may thereafter be proximally retracted from the patient, and the percutaneous and vascular access sites closed in accordance with conventional puncture closure techniques.

The anchor deployment catheter of the present invention may be readily used to accomplish any of a variety of anastomosis procedures, including attaching a synthetic vascular graft to an attachment site within a vessel, and performing tissue-to-tissue anastomosis of an autologous vein graft such as a graft of the saphenous vein into the coronary artery. The anastomosis catheter embodiment may also be utilized to provide intermediate support for a synthetic graft which has already been positioned at treatment site in a vessel.

Figure 12:
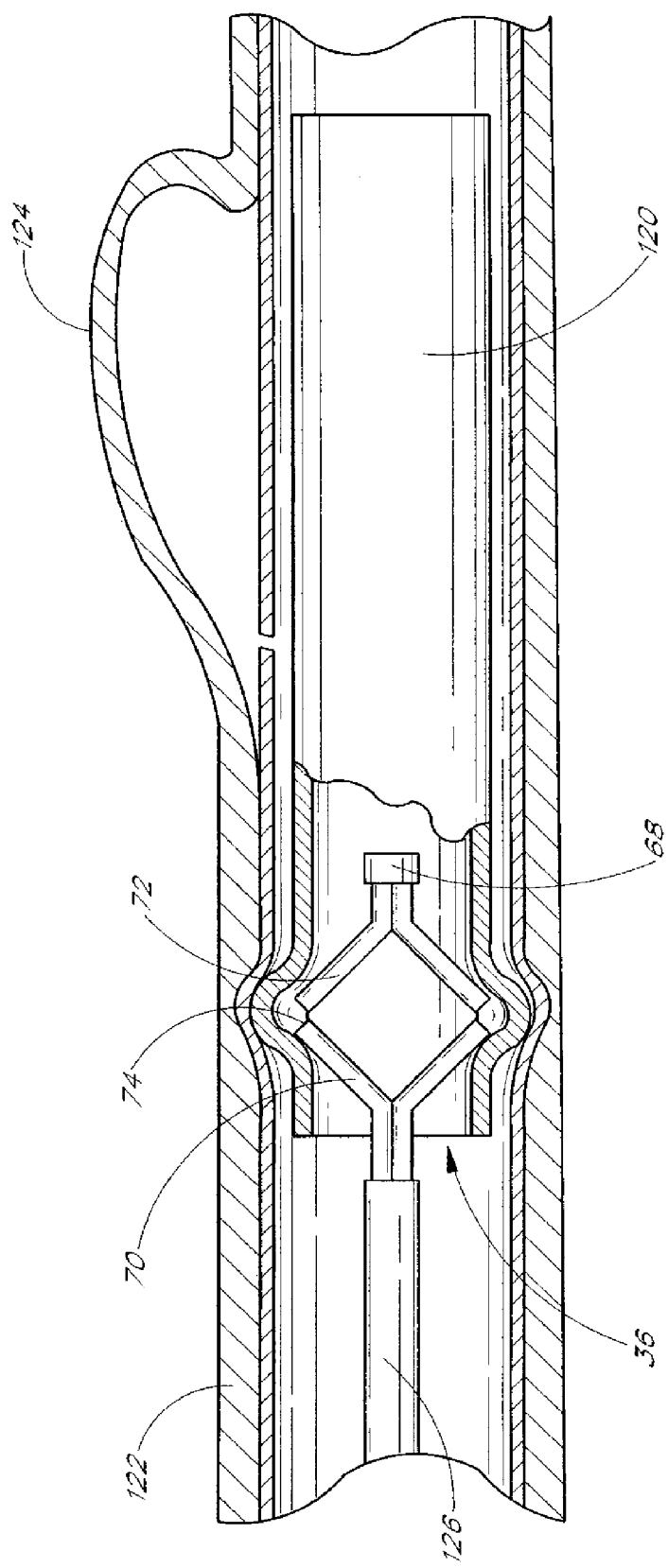
FIG. 12 is a schematic cross-sectional view of an anastomosis catheter positioned within a synthetic tubular graft at a site in a body lumen.

Referring to FIG. 12, there is illustrated a schematic side elevational cross-section of a vessel 122 having a defect 124 such as an aneurysm. A graft 120 is illustrated spanning the defect 124, and overlapping at least a portion of healthy vessel wall both proximally and distally of the aneurysm 124.

An anastomosis catheter 126 is illustrated in position within a proximal end of the graft 120. The anastomosis catheter 126 is provided with a plurality of anchor supports 62 near a distal end 36 thereof. Each anchor support comprises a proximal section 70, a distal section 72 and a hinge point 74.

Figure 13:
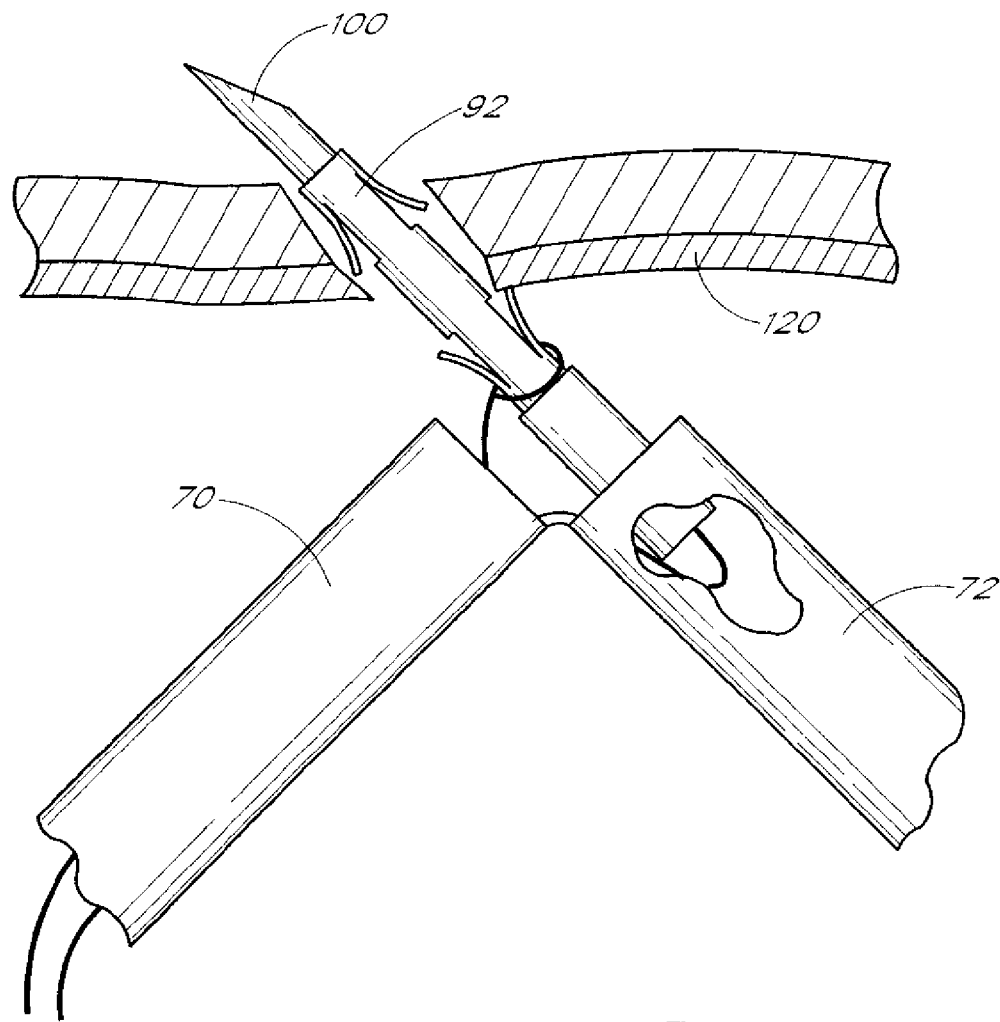
FIG. 13 is a schematic illustration as in FIG. 6A, with an anchor partially deployed through the graft and vessel wall.

Referring to FIG. 13, the graft 120 and vessel 122 have been penetrated by the sharpened tip 100 of an introducer 96, which has been deployed as discussed previously herein. The introducer 96 carries an anchor 92 thereon. In the illustrated embodiment, proximal traction on a deployment wire which has previously been discussed causes the introducer 96 to introduce the anchor 92 into the treatment site. Continued traction on the deployment wire retracts the introducer 96 into the proximal section 70 of the anchor support 62, leaving the anchor 92 in position.

Figure 14:
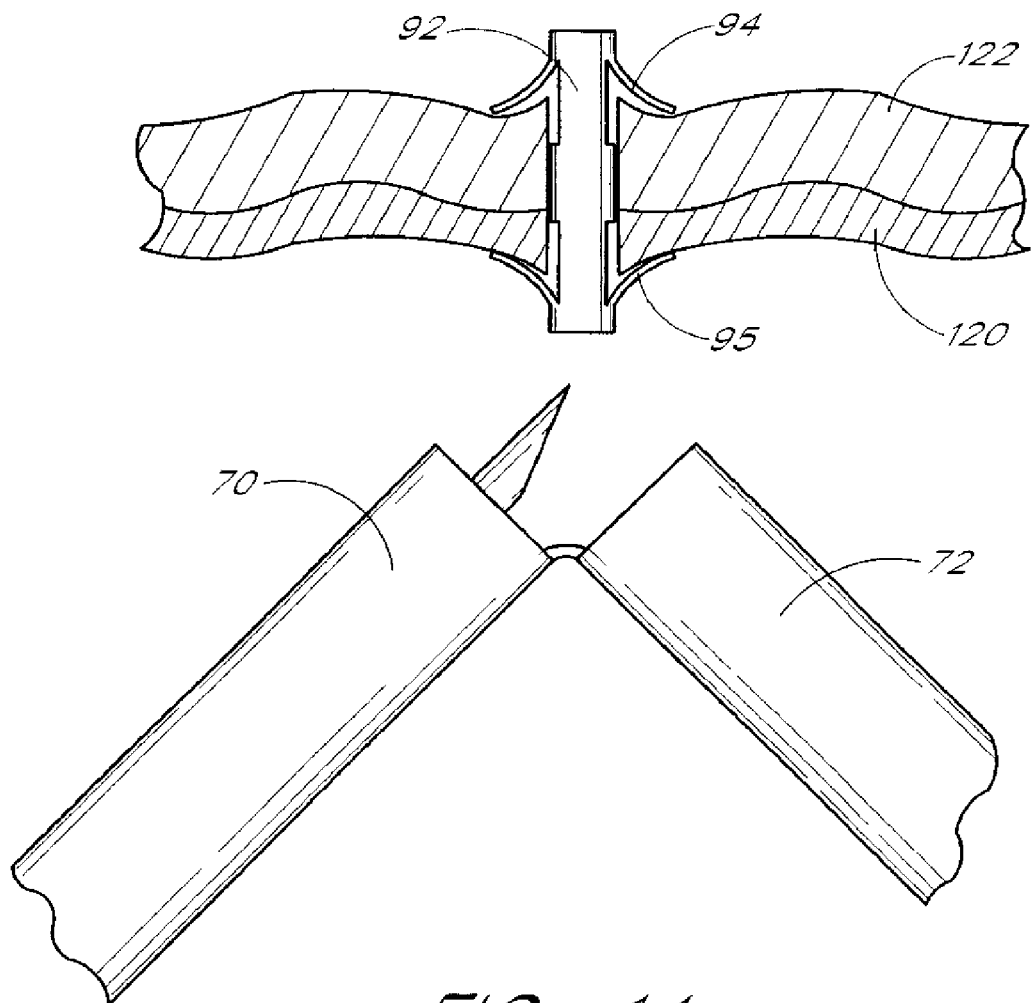
FIG. 14 is a schematic illustration as in FIG. 13, and similar to FIG. 6C, showing the anastomosis anchor fully deployed.

As illustrated in FIG. 14, the anchor 92 is provided with one or more distal barbs 94 for resisting proximal motion of the anchor 92, and one or more proximal barbs 95 for resisting distal migration of the anchor 92. In this manner, the anchor 92 will remain in position to secure the graft 120 to the vessel 122.

The anastomosis catheter 126 can be adapted for use in a variety of graft implantation and attachment methods. For example, a tubular graft which has been attached such as by the use of self expandable or balloon expandable stents at the proximal and distal ends of the graft may require intermediate support to maintain patency of the central lumen in between the axial ends. Intermediate support may be accomplished by either positioning additional stents within the tubular graft, or by using the anastomosis catheter 126 to anchor the graft to the native vessel wall. Two or more anchors may be provided in each anchor support. In this manner, the anastomosis catheter 126 may positioned at a first position where a first plurality of anchors are deployed through a graft into the native vessel, and then repositioned to a second position where a second plurality of anchors may be deployed to retain or secure the graft. Additional anchor supports and/or anchors may be provided on the anastomosis catheter 126, depending upon the number of anchors desirably positioned along the axial length of a graft.

Alternatively, the anastomosis catheter 126 may be utilized to implant a tubular graft. In this embodiment, the tubular graft is coaxially disposed about the exterior of the anastomosis catheter 126. The catheter is positioned at a treatment site, and the anchor supports are inclined to the axial orientation thereby positioning the vascular graft against the vessel wall. Anchors are deployed as has been discussed. The anchors may be secured to the graft directly such as through the use of a tether or other attachment structure, or may be independent from the graft but secured thereto in situ by the proximal and distal barbs or other structural arrangement which will become apparent to those of skill in the art in view of the disclosure herein. Thus, although referred to generally herein as an anastomosis catheter 126, this embodiment of the invention may also be considered a transluminal graft implantation catheter or graft attachment catheter as will be apparent to those of skill in the art.

Referring to FIGS. 15A-15G, there are illustrated a variety of tissue anchors which may be used in the tissue closure or attachment device of the present invention. Each of FIGS. 15A and 15B disclose an anchor having a body 92, a distal tip 101, and one or more barbs 94 to resist proximal movement of the anchor. An aperture 107 is provided to receive the anchor suture. The embodiments of FIGS. 15A and 15B can be readily manufactured such as by stamping or cutting out of flat sheet stock.

The anchor illustrated in FIG. 15C comprises a wire having a body 92 and a distal tip 101. The wire preferably comprises a super-elastic alloy such as Nitinol or other nickel titanium-based alloy. The anchor is carried within a tubular introducer, in a straight orientation, for introduction into the tissue where the anchor is to reside. As the body 92 is advanced distally from the carrier tube, the anchor resumes its looped distal end configuration within the tissue, to resist proximal retraction on the wire body 92.

FIG. 15D illustrates a tubular anchor, which may be manufactured from a section of hypotube, or in the form of a flat sheet which is thereafter rolled about a mandrel and soldered or otherwise secured. The anchor comprises a distal tip 101, one or more barbs 94, and an aperture 107 for securing the anchor suture. The anchor of FIG. 15D may be carried by and deployed from the interior of a tubular anchor support as has been discussed. Alternatively, the anchor of FIG. 15D can be coaxially positioned over a central tubular or solid anchor support wire.

Figures 15E, 15F:
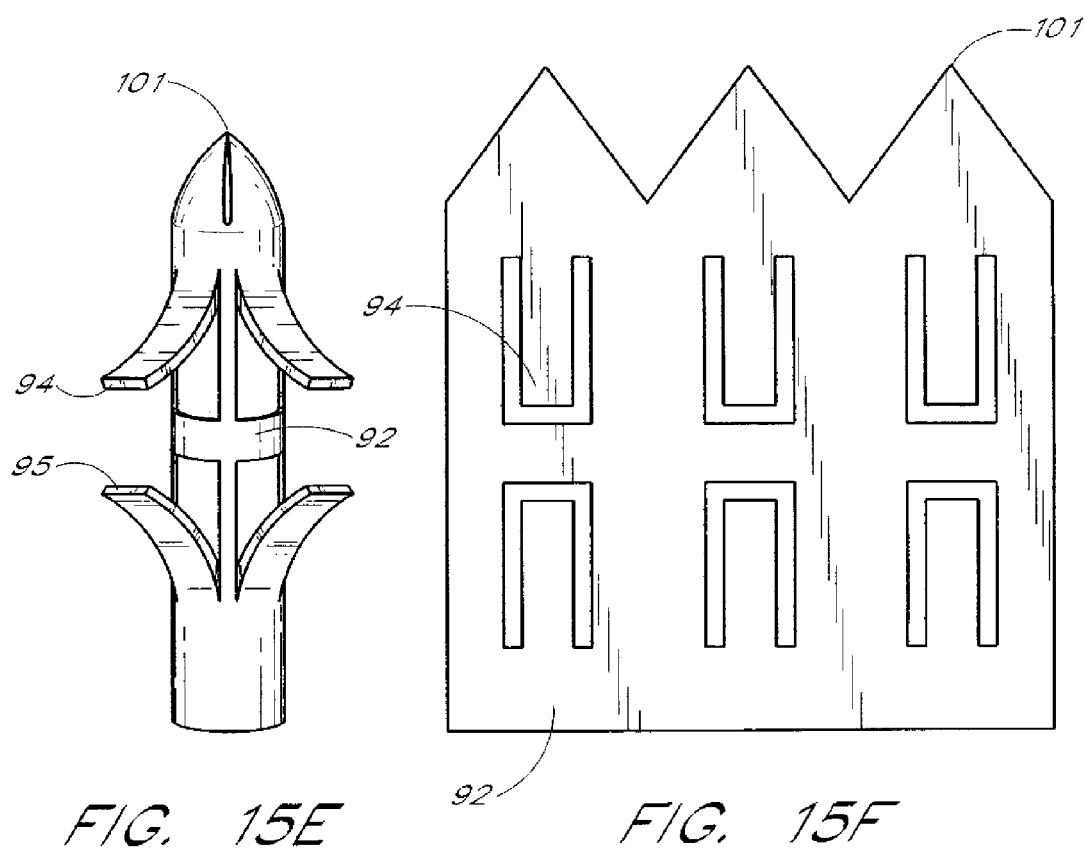
Figure 15G:
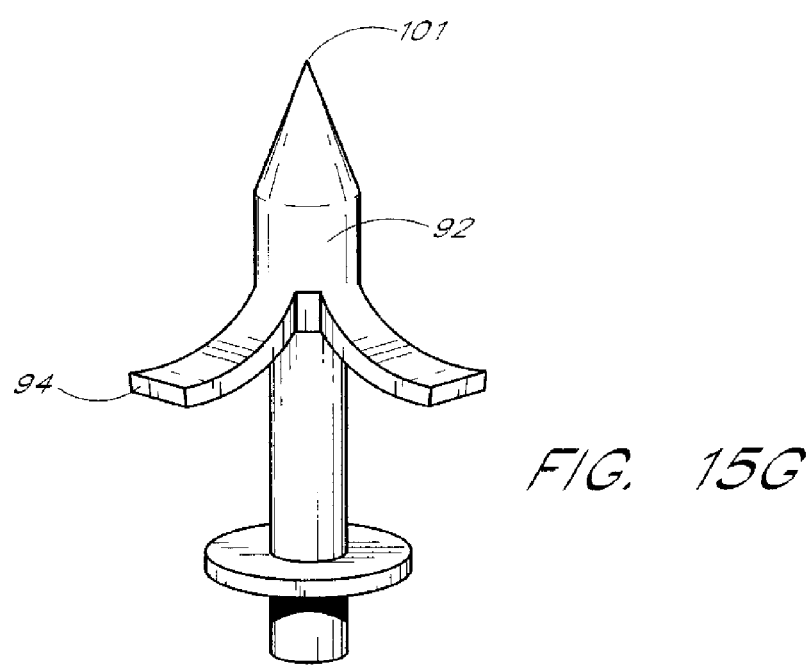

FIG. 15E illustrates an anchor which may be formed either by cutting from tube stock or by cutting a flat sheet such as illustrated in FIG. 15F which is thereafter rolled about an axis and soldered or otherwise secured into a tubular body. In this embodiment, three distal tips 101 in the flat sheet stock may be formed into a single distal tip 101 in the finished anchor as illustrated in FIG. 15E. One or more barbs 94 may be formed by slotting the sheet in a U or V-shaped configuration as illustrated. The anchor in FIG. 15E is additionally provided with one or more barbs 95 which resist distal migration of the anchor. This may be desirable where the anchor is implanted across a thin membrane such as attachment of a synthetic graft, or in other applications such as tissue-to-tissue anastomosis where distal as well as proximal migration is desirably minimized.

Referring to FIGS. 16 through 18, there is disclosed an alternate anastomosis anchor 90 in accordance with the present invention. Anchor 90 comprises a proximal end 130, a distal end 132 and a central lumen 134 extending therebetween. Central lumen 134 allows the anchor 90 to be positioned on an introducer 96 as is illustrated in FIG. 17, and has been previously discussed.

The anchor 90 is provided with at a least first proximal projection 136 and a second proximal projection 138. First and second proximal projections 136 and 138 are designed to enlarge radially outwardly in response to axial shortening of the anchor 90. Thus, in an axially elongated configuration such as that illustrated in FIG. 17, the first and second proximal projections 136 and 138 extend generally in parallel with the longitudinal axis of the anchor 90. A distally facing tissue contact surface 144 is forced to incline radially outwardly in response to axial shortening of the anchor 90, as will be apparent to those of skill in the art in view of the illustration in FIG. 16. Although illustrated with two proximal projections positioned at approximately 180.degree. apart from each other, three or four or more proximal projections may be provided, preferably evenly distributed about the circumference of the anchor 90.

At least a first distal projection 140, and preferably a second distal projection 142 are provided on the tubular body 92 spaced distally apart from the proximal projections. First and second distal projections 140 and 142 similarly expand or enlarge radially outwardly in response to axial compression or other shortening of the anchor 90. Axial separation between the first proximal projection 136 and first distal projection 140 allows the anchor 90 to secure a graft 126 or other structure to the interior wall of the vessel 120 or other tissue plane as illustrated in FIG. 18, by sandwiching the wall of the graft 126 and vessel wall 120 between distally facing tissue contact surface 144 and proximally facing tissue contact surface 146. The anchor 90 can be deployed from the introducer 96, utilizing any of the deployment catheters disclosed elsewhere herein.

The radial enlargement of the proximal and distal projections is accomplished by axially shortening the anchor 90 along its longitudinal axis. This may be accomplished by axially compressing a compression actuated embodiment, by releasing a restraint on a biased embodiment, or by activating a memory metal embodiment such as by exposing it to a current or temperature change.

In a compression actuated embodiment, proximal movement of proximal end 130 is inhibited by seating the proximal end 130 against a stop surface such as on the proximal section 98 of an introducer 96, as illustrated in FIG. 17. The distal end 132 is thereafter advanced proximally, such as by proximal traction on a proximal force transmitter 148 which may be a suture 150. Suture 150 may extend in a loop through a plurality of apertures 152, extending through the proximal and distal projections. Alternatively, the suture 150 may extend alongside the anchor 90 or through central lumen 134 depending upon the tolerance between the central lumen 134 and the introducer 96. Alternative proximal force transmitter structures such as pull wires and moveable cores may also be utilized, as will be apparent to those of skill in the art.

The anchor 90 may be manufactured in a variety of ways, such as by cutting or etching from a metal or polymeric tube. Preferably, the anchor 90 is laser cut from a Nitinol or steel tube having an outside diameter within the range of from about 0.014" to about 0.038" and an axial length within the range of from about 0.050" to about 0.250. The axial length of each of the distally facing tissue contact surface 144 and proximally facing tissue contact 146 is within the range of from about 0.010" to about 0.060". The wall thickness of the tube is within the range of from about 0.002" to about 0.012". Full axial compression of most metal tube embodiments will bend the metal beyond its elastic limit at each apex on the various projections, such that the suture 150 may be removed from the anchor 190 following deployment and the anchor will remain in its deployed (axially compressed) configuration as illustrated in FIG. 18.

In a biased embodiment, the anchor may be formed from a memory metal such as a NiTi alloy in the form illustrated in FIG. 18. The anchor is reduced to its introduction crossing profile by axial elongation and retained in that form by axial traction or by capture within a removable tubular sleeve. Once deployed from the tubular catheter body or other restraining structure, or upon removal of the axial traction, the anchor assumes the deployed configuration illustrated in FIG. 20.

Although the present invention has been described in terms of certain preferred embodiments, other embodiments will become apparent to those of skill in the art in view of the disclosure herein. Accordingly, the scope of the invention is not intended to be limited by the specific disclosed embodiments, but, rather, by the attached claims.

What is claimed is:

1. A method of attaching a tubular graft to a vessel wall, comprising the steps of:
    positioning a tubular graft within a vessel;
    positioning a catheter within the graft, the catheter comprising:
        at one introducer, the introducer having a distal end; and
        at least one anchor having a proximal end, a distal end and a first length extending between the proximal end and the distal end;
    holding the graft against the vessel wall; and
    deploying the anchor through the graft and into the vessel wall, wherein the anchor is shortened from the first length to a second length to secure the graft to the vessel wall.

2. The method of claim 1, wherein the anchor is deployed distally from the distal tip of the introducer.

3. The method of claim 1, wherein the distal tip of the introducer is a sharpened tip.

4. The method of claim 1, wherein when the anchor is shortened, a radial cross-section of the anchor expands.

5. The method of claim 4, wherein the anchor comprises a body having a proximal end and a distal end, a proximal arm extending proximally from the proximal end of the body and a distal arm extending distally from the distal end of the body, and wherein the proximal arm and the distal arm move relative to the body when the anchor is shortened.

6. The method of claim 1 wherein the anchor is biased to an expanded position.

7. The method of claim 1 further comprising the step of inclining the introducer relative to an axis of the catheter prior to the step of deploying the anchor.

8. The method of claim 7 wherein the catheter comprises a second introducer having a distal end and a second anchor and wherein during the step of inclining the introducer, the second introducer is inclined at a different angle relative to the axis of the catheter.

9. The method of claim 1 wherein the catheter further comprises at least one anchor support corresponding to the at least one introducer and further comprising the step of deploying the introducer from within the anchor support.

10. A method of attaching a tubular graft to a vessel wall, comprising the steps of:
    positioning a tubular graft within a vessel;
    positioning a catheter within the graft, the catheter comprising at least one anchor;
    holding the graft against the vessel wall; and
    deploying the anchor through the graft and into the vessel wall to secure the graft to the vessel wall;
    wherein the anchor comprises an anchor body having a first position in which the cross-section of the anchor is minimized and a second position in which the cross-section is expanded and configured to resist proximal and distal movement when deployed through the graft and secured to the vessel wall.

11. The method of claim 10 wherein the anchor is longer in the first position than in the second position.

12. The method of claim 10 wherein the anchor comprises a body having a proximal end and a distal end, a first proximal arm extending proximally from the proximal end of the body and a first distal arm extending distally from the distal end of the body, and wherein the proximal arm and the distal arm move relative to the body when the anchor moves from the first position to the second position.

13. The method of claim 12 wherein the anchor further comprises a second proximal arm extending proximally from the proximal end of the body and a second distal arm extending distally from the distal end of the body.

14. The method of claim 10 wherein the anchor is biased to the second position.

15. The method of claim 10 wherein the step of deploying the anchor comprises the step of moving the anchor to the second position.

16. The method of claim 10 wherein the step of deploying the anchor comprises the step of deploying the anchor from within the catheter.

* * * * *